US010913972B2

(12) United States Patent
Encell et al.

(10) Patent No.: US 10,913,972 B2
(45) Date of Patent: *Feb. 9, 2021

(54) 5,5-DISUBSTITUTED LUCIFERINS AND THEIR USE IN LUCIFERASE-BASED ASSAYS

(71) Applicant: Promega Corporation, Madison, WI (US)

(72) Inventors: Lance P. Encell, Fitchburg, WI (US); Mary P. Hall, Waunakee, WI (US); Michael Killoran, Fitchburg, WI (US); Thomas A. Kirkland, Atascadero, CA (US); Poncho Meisenheimer, San Luis Obispo, CA (US); Ce Shi, San Luis Obispo, CA (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/516,974

(22) Filed: Jul. 19, 2019

(65) Prior Publication Data

US 2019/0338340 A1 Nov. 7, 2019

Related U.S. Application Data

(63) Continuation of application No. 15/829,581, filed on Dec. 1, 2017, now Pat. No. 10,400,264.

(60) Provisional application No. 62/428,707, filed on Dec. 1, 2016.

(51) Int. Cl.
| | |
|---|---|
| *A61K 51/04* | (2006.01) |
| *A61K 51/00* | (2006.01) |
| *C12Q 1/66* | (2006.01) |
| *C07D 417/04* | (2006.01) |
| *G01N 21/76* | (2006.01) |
| *C07D 513/10* | (2006.01) |
| *C07D 513/04* | (2006.01) |
| *C07D 277/66* | (2006.01) |
| *A61K 49/00* | (2006.01) |

(52) U.S. Cl.
CPC .............. *C12Q 1/66* (2013.01); *A61K 49/003* (2013.01); *A61K 51/00* (2013.01); *A61K 51/04* (2013.01); *C07D 277/66* (2013.01); *C07D 417/04* (2013.01); *C07D 513/04* (2013.01); *C07D 513/10* (2013.01); *G01N 21/763* (2013.01)

(58) Field of Classification Search
CPC ...... C12Q 1/66; C07D 277/66; C07D 417/04; C07D 513/10; C07D 513/04; C07D 277/62; C07D 277/08; G01N 21/763; A61K 49/00; A61K 49/0002; A61K 49/0004; A61K 49/001; A61K 49/003; A61K 49/0013; A61K 49/0015; A61K 49/0017; A61K 49/0019; A61K 49/0021; A61K 51/00; A61K 51/04
USPC ...... 424/1.11, 1.65, 1.69, 9.1, 9.2, 9.6, 1.49; 548/146, 152
See application file for complete search history.

(56) References Cited

U.S. PATENT DOCUMENTS

| | | | |
|---|---|---|---|
| 8,367,842 B2* | 2/2013 | Akhavan-Tafti | .......... C09B 7/00 548/178 |
| 10,400,264 B2* | 9/2019 | Encell | ................... G01N 21/763 |
| 2004/0248255 A1 | 12/2004 | Ryu et al. | |
| 2007/0015790 A1 | 1/2007 | Cali et al. | |
| 2014/0304842 A1 | 10/2014 | Hitko | |
| 2019/0040449 A1 | 2/2019 | Shi et al. | |

FOREIGN PATENT DOCUMENTS

| | | |
|---|---|---|
| EP | 1008600 A2 | 6/2000 |
| WO | WO 2006130551 A2 | 12/2006 |
| WO | WO 2011008912 A1 | 1/2011 |
| WO | WO 2014159044 A1 | 10/2014 |

OTHER PUBLICATIONS

Branchini et al., "Yellow-Green and Red Firefly Bioluminescence from 5,5-Dimethylosyluciferin," J Am Chem Soc, 2002, 124(10): 2112-2113.
Hirano et al., "Spectroscopic studies of the color modulation mechanism of firefly (beetle) bioluminescence with amino-analogs of luciferin and oxyluciferin," Photochemical & Photobiological Sciences, 2012, 11:1281-1284.
Chemical Abstracts Registry No. 18330-81-9, indexed in the Registry file on STN CAS Online Nov. 16, 2018.
IUPAC 1974 Recommendations for Section E: Stereochemistry, Rules for the Nomeclature of Organic Chemistry, Pure Appl. Chem., 1976,45:11-30.
Mofford, et al., "Aminoluciferins extend firefly luciferase bioluminescence into the near-infrared and can be preferred substrates over D-luciferin," J. Am. Chem. Soc. 2014, 136, 13277-13282.
Rothweiler et al., "Luciferin and derivatives as a DYRK selective scaffold for the design of protein kinase inhibitors," European Journal of Medical Chemistry, 2015, 94:140-148.
Stanfield et al., "Preparation of β,β-Dialkyl analogs of cysteine suitable for peptide synthesis," J. Org. Chem. 1986, 51: 5153-5156.
Viviani et al., "Bioluminescence of Beetle Luciferases with 6'-Amino-D-luciferin Analogues Reveals Excited Keto-oxyluciferin as the Emitter and Phenolate/Luciferin Binding Site Interactions Modulate Bioluminescence Colors," Biochemistry, 2014, 53:5208-5220.
Viviani et al., "The Luciferin Binding Site Residues C/T311 (S314) Influence the Bioluminescence Color of Beetle Luciferases through Main-Chain Interaction with Oxyluciferin Phenolate," Biochemistry, 2013, 52(1):19-27.

(Continued)

*Primary Examiner* — D. L. Jones
(74) *Attorney, Agent, or Firm* — Casimir Jones, S.C.; Anne M. Reynolds

(57) ABSTRACT

Described are luciferin analogues, methods for making the analogues, kits including the analogues, and methods of using the compounds for the detection of luminescence in luciferase-based assays.

23 Claims, 18 Drawing Sheets

Specification includes a Sequence Listing.

(56) References Cited

OTHER PUBLICATIONS

Woodroofe, et al., "N-Aikylated 6'-aminoluciferins are bioluminescent substrates for Ultra-Gio and Quantilum luciferase: new potential scaffolds for bioluminescent assays," Biochemistry, 2008, 47, 10383-10393.
International Search Report and Written Opinion for Application No. PCT/US2017/064284 dated Jan. 30, 2018 (15 pages).

* cited by examiner

D-luciferin

"G1" Ring   "G2" Ring   "G3" Ring

Dehydroluciferin

D-III-a, L-III-a

D-III-b, L-III-b

SEQUENCE LISTING

<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Synthetic carboxybenzyl group

<400> SEQUENCE: 1

Asp Glu Val Asp
1

<210> SEQ ID NO 2

```
<211> LENGTH: 4
<212> TYPE: PRT
<213> ORGANISM: Artificial Sequence
<220> FEATURE:
<223> OTHER INFORMATION: Synthetic carboxybenzyl group

<400> SEQUENCE: 2

Leu Glu Thr Asp
1

<210> SEQ ID NO 3
<211> LENGTH: 6
<212> TYPE: PRT
<213> ORGANISM: Artificial Sequence
<220> FEATURE:
<223> OTHER INFORMATION: Synthetic succinyl group

<400> SEQUENCE: 3

Gly Pro Leu Leu Val Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic carboxybenzyl group

<400> SEQUENCE: 4

Glx Asn Leu Pro Asn Leu Asp
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic carboxybenzyl group

<400> SEQUENCE: 5

Gln Glu Val Tyr
1

<210> SEQ ID NO 6
<211> LENGTH: 7
<212> TYPE: PRT
<213> ORGANISM: Artificial Sequence
<220> FEATURE:
<223> OTHER INFORMATION: Synthetic carboxybenzyl group

<400> SEQUENCE: 6

Val Pro Val Asp Val Ala Asp
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic carboxybenzyl group

<400> SEQUENCE: 7

Val Glu Ile Asp
1

<210> SEQ ID NO 8
<211> LENGTH: 4
```

<212> TYPE: PRT
<213> ORGANISM: Artificial Sequence
<220> FEATURE:
<223> OTHER INFORMATION: Synthetic carboxybenzyl group

<400> SEQUENCE: 8

Ala Thr Ala Asp
1

<210> SEQ ID NO 9
<211> LENGTH: 4
<212> TYPE: PRT
<213> ORGANISM: Artificial Sequence
<220> FEATURE:
<223> OTHER INFORMATION: Synthetic carboxybenzyl group

<400> SEQUENCE: 9

Ile Glu Pro Asp
1

<210> SEQ ID NO 10
<211> LENGTH: 4
<212> TYPE: PRT
<213> ORGANISM: Artificial Sequence
<220> FEATURE:
<223> OTHER INFORMATION: Synthetic carboxybenzyl group

<400> SEQUENCE: 10

Ile Glu Thr Asp
1

<210> SEQ ID NO 11
<211> LENGTH: 6
<212> TYPE: PRT
<213> ORGANISM: Artificial Sequence
<220> FEATURE:
<223> OTHER INFORMATION: Synthetic carboxybenzyl group

<400> SEQUENCE: 11

Thr Ser Ala Val Leu Gln
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic carboxybenzyl group

<400> SEQUENCE: 12

Val Asn Ser Thr Leu Gln
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic norLeucine

<400> SEQUENCE: 13

Asp Glu Val Asp
1

5,5-DISUBSTITUTED LUCIFERINS AND THEIR USE IN LUCIFERASE-BASED ASSAYS

CROSS-REFERENCE TO RELATED APPLICATIONS

This application is a continuation of U.S. patent application Ser. No. 15/829,581, filed on Dec. 1, 2017, now U.S. Pat. No. 10,400,264, issue don Sep. 3, 2019, which claims priority to U.S. Provisional Patent Application No. 62/428,707, filed on Dec. 1, 2016, the entire contents of which are incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,501 Byte ASCII (Text) file named "2020-08-14_37148-303_SQL_ST25" created on Aug. 14, 2020.

TECHNICAL FIELD

The present disclosure relates to luciferin analogues, methods for making luciferin analogues, and methods of using luciferin analogues in luciferase-based assays.

BACKGROUND

Bioluminescent assays are used extensively in the investigation of cellular physiology, especially processes associated with gene expression. In particular, luciferase reporter enzymes are quite valuable tools in this field, and, to date, there has been intense protein engineering to obtain small and environmentally insensitive luciferases that may be useful in bioluminescent assays. There exist a number of efficient luciferase reporters that enable whole-cell biosensor measurements, drug discovery through high-throughput screening, and in vivo imaging that also permit the study of protein-protein interactions in living cells, apoptosis, and cell viability. Luciferases that use luciferin and luciferin analogues as substrates are widely used systems due to their brightness and acceptance in whole cell applications. Firefly luciferase and various beetle luciferases, for example, produce luminescence in the presence of luciferin, magnesium ions, oxygen, and ATP.

SUMMARY OF THE INVENTION

In one aspect, disclosed are 5,5-disubstituted luciferins or luciferin analogues. Also disclosed are methods of making the compounds, kits comprising the compounds, and methods of using the compounds as luciferase substrates in luciferase-based assays. Also disclosed are detection systems including one or more luciferases and one or more 5,5-disubstituted luciferin analogues.

DETAILED DESCRIPTION

Figure 1:
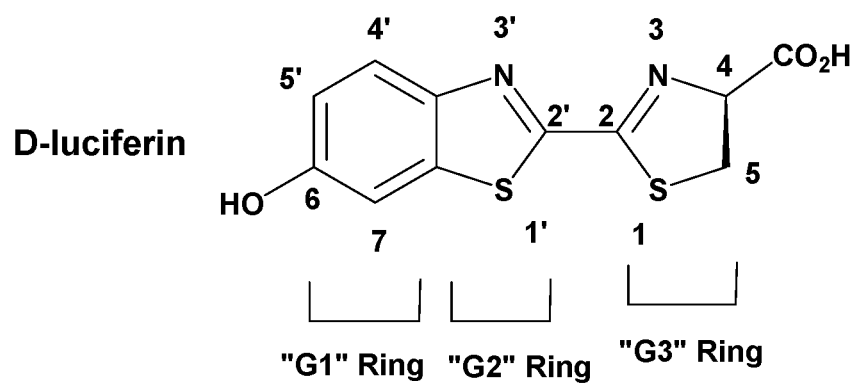
FIG. 1 shows the structures of D-luciferin and dehydroluciferin with the numbering of ring atoms.
Figure 1:
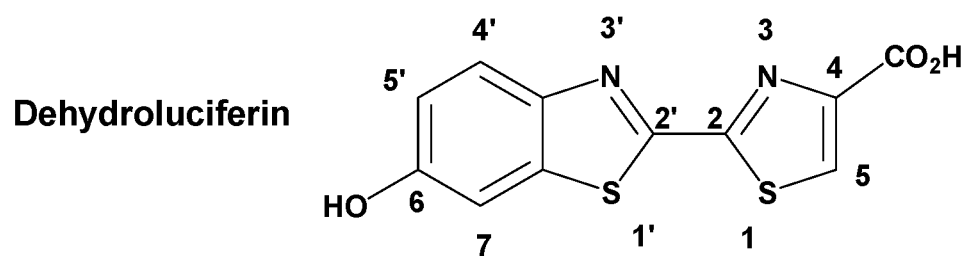

D-luciferin (FIG. 1) is the natural substrate for firefly and click beetle luciferases and can be used as a substrate in bioluminescent assays employing luciferase reporter enzymes. However, D-luciferin is thermally unstable and decomposes over time in stock solutions at ambient temperature. Dehydroluciferins have been identified as degradation products of luciferins. These dehydroluciferins are potent inhibitors of luciferases and can lead to decreased light output in luciferase-based bioluminescent assays. There exists a need for luciferin analogues which have improved thermally stability while retaining light producing activity in luciferase assays.

In one aspect, disclosed are 5,5-disubstituted luciferins analogues. The disclosed compounds may exhibit unexpected thermal stability and may provide for a luciferase detection system that is free of inhibition caused by luciferin decomposition products. The disclosed compounds may be especially useful for applications that require luciferins to be stored in solutions at ambient temperature over long period of time. The disclosed compounds may also provide for a long duration time in many live cell bioluminescent assays or live cell imaging methods.

The disclosed compounds may be substrates for a luciferase enzyme that utilize luciferin ("luciferin-utilizing enzymes") to produce luminescence, including, but not limited to, luciferases and photoproteins found in various organisms such as beetles (e.g., *Photinus pyralis* and *Photuris pennsylvanica* (fireflies of North America), *Pyrophorus plagiophthalamus* (the Jamaican click beetle)), *Renilla reniformis* (the sea pansy), and several bacteria (e.g., *Xenorhabdus luminescens* and *Vibrio* spp).

5,5-disubstituted luciferins are historically considered incapable of producing light via firefly luciferase mediated processes. Specifically, 5-5-disubstituted luciferins are commonly believed to produce light only via chemiluminescent processes, not via enzymatic processes (e.g., by firefly luciferases). The disclosed compounds, surprisingly, are able to be utilized by firefly luciferases and click beetle luciferases to produce luminescence via enzymatic processes. Further, luciferases can effectively utilize various stereoisomeric forms and mixtures (e.g., L- and D-forms) of the 5,5-disubstituted luciferin analogues to produce bioluminescence, and can operate over a broad pH range. This enables the use of racemates in applications where racemization can compromise signal stabilities.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a hydrocarbon chain containing from 2 to 10 carbon atoms with at least one carbon-carbon double bond. The alkenyl group may be substituted or unsubstituted. For example, the alkenyl group may be substituted with an aryl group, such as a phenyl.

The term "alkynyl" as used herein, means a hydrocarbon chain containing from 2 to 10 carbon atoms with at least one carbon-carbon triple bond. The alkynyl group may be substituted or unsubstituted. For example, the alkynyl group may be substituted with an aryl group, such as a phenyl.

The term "alkoxyalkyl" as used herein, refers to an alkoxy group, as defined herein, appended to the parent molecular moiety through an alkyl group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "amino acid" refers to both natural and unnatural amino acids. It also includes protected natural and unnatural amino acids.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. "Cycloalkyl" also includes carbocyclic ring systems in which a cycloalkyl group is appended to the parent molecular moiety and is fused to an aryl group as defined herein, a heteroaryl group as defined herein, or a heterocycle as defined herein.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms have been replaced by a heteroatom selected from S, Si, O, P and N. The heteroatom may be oxidized. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocycle" or "heterocyclic" as used herein means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" as used herein, means an —OH group.

The term "hydroxyalkyl" as used herein, means an alkyl group, as defined herein, in which one, two, three, four, five, six, seven or eight hydrogen atoms are replaced by a hydroxyl group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

An "ATP detection mixture" contains materials that will allow for the detection of ATP in a sample. The materials needed, and the particular concentrations and/or amounts, of the materials needed to generate a luminescent signal will vary depending on the luciferase enzyme used as well as the type of luciferase-based assay being performed. In general, for beetle luciferases, these materials can include: magnesium ($Mg^{2+}$) salt, such as magnesium sulfate, a luciferase enzyme, e.g., UltraGlo luciferase (Promega Corporation), and a luciferase substrate, e.g., luciferin, luciferin derivative, functional analog, or novel luciferin derivative capable of generating light when the luciferase substrate, e.g., luciferin derivative disclosed herein, is used as a substrate for the beetle luciferase. Often other materials will be added to the solution including: a buffer to maintain the reaction at the proper pH, an additive such as PRIONEX or Bovine serum albumin (BSA) to help maintain luciferase activity, reducing agents, detergents, esterases, salts, amino acids, e.g., D-cysteine, etc. An example luciferase detection mixture would contain a luciferase enzyme, a luciferase substrate, $MgSO_4$, Tergitol NP-9, and Tricine.

A "luciferase detection mixture" contains materials that will allow for the detection of a luciferase enzyme. The materials needed, and the particular concentrations and/or amounts, of the materials needed to generate a luminescent signal will vary depending on the luciferase enzyme used as well as the type of luciferase-based assay being performed. In general, for beetle luciferases, these materials can include: ATP, magnesium (Mg') salt, such as magnesium sulfate, and a luciferase substrate, e.g., luciferin, luciferin derivative, functional analog, or novel luciferin derivative capable of generating light when the luciferase substrate, e.g., luciferin derivative disclosed herein, is used as a substrate for the beetle luciferase. Often other materials will be added to the solution including: a buffer to maintain the reaction at the proper pH, an additive such as PRIONEX or Bovine serum albumin (BSA) to help maintain luciferase activity, reducing agents, detergents, esterases, salts, amino acids, e.g. D-cysteine, etc. An example luciferase detection mixture would contain a luciferase substrate, $MgSO_4$, ATP, Tergitol NP-9, and Tricine.

A "luciferase reaction mixture" contains a luciferase enzyme and materials that will allow the luciferase enzyme to generate a light signal. The materials needed, and the particular concentrations and/or amounts, of the materials needed to generate a luminescent signal will vary depending on the luciferase enzyme used as well as the type of luciferase-based assay being performed. In general, for beetle luciferases, these materials can include: ATP, magnesium ($Mg^{2+}$) salt, such as magnesium sulfate, a beetle luciferase enzyme, and a luciferin or novel luciferin derivative capable of generating light when the luciferin or novel luciferin derivative is used as a substrate for the beetle luciferase. Often other materials will be added to the solution including: a buffer to maintain the reaction at the proper pH, an additive such as PRIONEX or Bovine serum albumin (BSA) to help maintain luciferase activity, reducing agents, detergents, esterases, salts, amino acids, e.g. D-cysteine, etc. An example luciferase reaction mixture would contain a beetle luciferase, $MgSO_4$, ATP, Tergitol NP-9, and Tricine.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

Disclosed are compounds of formula (I'):

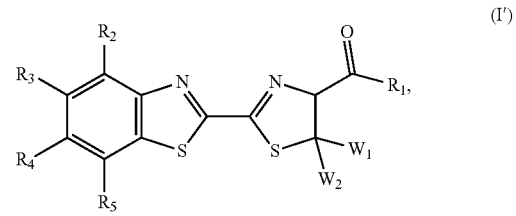

(I')

or a tautomer, or a salt thereof, wherein $R_1$ is hydrogen, halogen, alkyl, alkenyl, alkynyl, heteroalkyl, aryl, heteroaryl, heterocycle, cycloalkyl, cycloalkenyl, —$OR_{1a}$, —$NR_{1b}R_{1c}$, —$OG^1$, —$NR_{1x}G^1$, or —$NR_{1x}G^{10}$;

$R_2$ is hydrogen, halogen, cyano, nitro, alkyl, alkenyl, alkynyl, heteroalkyl, aryl, heteroaryl, heterocycle, cycloalkyl, cycloalkenyl, —$OR_{2a}$, —$NR_{2b}R_{2c}$, —$SR_{2d}$, —$SO_2R_{2e}$, —$S(O)R_{2f}$, —$P(O)OR_{2g}R_{2h}$, —$OG^1$, or —$NR_{2x}G^1$;

$R_3$ is hydrogen, halogen, cyano, nitro, alkyl, alkenyl, alkynyl, heteroalkyl, aryl, heteroaryl, heterocycle, cycloalkyl, cycloalkenyl, —$OR_{3a}$, —$NR_{3b}R_{3c}$, —$SR_{3d}$, —$SO_2R_{3e}$, —$S(O)R_{3f}$, —$P(O)OR_{3g}R_{3h}$, —$OG^1$, or —$NR_{3x}G^1$;

$R_4$ is hydrogen, halogen, cyano, nitro, alkyl, alkenyl, alkynyl, heteroalkyl, aryl, heteroaryl, heterocycle, cycloalkyl, cycloalkenyl, —$OR_{4a}$, —$NR_{4b}R_{4c}$, —$SR_{4d}$, —$SO_2R_{4e}$, —$S(O)R_{4f}$, —$P(O)OR_{4g}R_{4h}$, —$OG^1$, or —$NR_{4x}G^1$;

$R_5$ is hydrogen, halogen, cyano, nitro, alkyl, alkenyl, alkynyl, heteroalkyl, aryl, heteroaryl, heterocycle, cycloalkyl, cycloalkenyl, —$OR_{5a}$, —$NR_{5b}R_{5c}$, —$SR_{5d}$, —$SO_2R_{5e}$, —$S(O)R_{5f}$, —$P(O)OR_{5g}R_{5h}$, —$OG^1$, or —$NR_{5x}G^1$;

or $R_2$ and $R_3$ together with the atoms to which they are attached, $R_3$ and $R_4$ together with the atoms to which they are attached, or $R_4$ and $R_5$ together with the atoms to which they are attached, form a 5- or 6-membered saturated, partially unsaturated or fully unsaturated ring, the 5- or 6-membered ring optionally containing 1, 2 or 3 heteratoms or heteroatom groups each independently selected from the group consisting of O, N, S, NO, SO and $SO_2$ as ring members, the 5- or 6-membered ring optionally fused to an aryl, heteroaryl, heterocycle, or cycloalkyl, the 5- or 6-membered ring substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, acyl, —OG$^1$, -NHG$^1$, and —N(C$_1$-C$_{10}$alkyl)G$^1$;

$R_{1a}$, $R_{1b}$, $R_{1c}$, $R_{2a}$, $R_{2b}$, $R_{2c}$, $R_{2d}$, $R_{2e}$, $R_{2f}$, $R_{2g}$, $R_{2h}$, $R_{3a}$, $R_{3b}$, $R_{3c}$, $R_{3d}$, $R_{3e}$, $R_{3f}$, $R_{3g}$, $R_{3h}$, $R_{4a}$, $R_{4b}$, $R_{4c}$, $R_{4d}$, $R_{4e}$, $R_{4f}$, $R_{4g}$, $R_{4h}$, $R_{5a}$, $R_{5b}$, $R_{5c}$, $R_{5d}$, $R_{5e}$, $R_{5f}$, $R_{5g}$, and $R_{5h}$, are each independently selected from the group consisting of hydrogen, alkyl, alkenyl, alkynyl, heteroalkyl, aryl, heteroaryl, heterocycle, cycloalkyl, and cycloalkenyl;

$R_{1x}$, $R_{2x}$, $R_{3x}$, $R_{4x}$, and $R_{5x}$ are each independently hydrogen or $C_1$-$C_{12}$alkyl;

G$^1$ comprises a substrate of a first enzyme, wherein biotransformation of the substrate by the first enzyme converts G$^1$ to H;

—NR$_{1x}$G$^{10}$ is a group that is cleavable by a second enzyme to convert the —NR$_{1x}$G$^{10}$ group to —OH; and W$_1$ and W$_2$ are each independently selected from the group consisting of alkyl, alkenyl, alkynyl, alkoxy, heteroalkyl, aryl, heteroaryl, heterocycle, cycloalkyl, and cycloalkenyl; or W$_1$ and W$_2$ together with the carbon to which they are attached form a cycloalkyl, cycloalkenyl, or heterocycle;

wherein said alkyl, alkenyl, alkynyl, alkoxy, heteroalkyl, aryl, heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In some embodiments, formula (I') is formula (I):

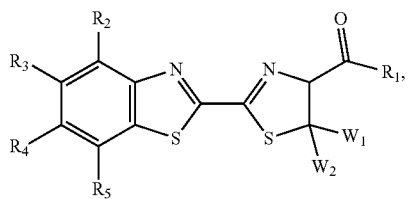

(I)

or a tautomer, or a salt thereof, wherein

R$_1$ is hydrogen, halogen, alkyl, alkenyl, alkynyl, heteroalkyl, aryl, heteroaryl, heterocycle, cycloalkyl, cycloalkenyl, —OR$_{1a}$, or —NR$_{1b}$R$_{1c}$;

R$_2$ is hydrogen, halogen, cyano, nitro, alkyl, alkenyl, alkynyl, heteroalkyl, aryl, heteroaryl, heterocycle, cycloalkyl, cycloalkenyl, —OR$_{2a}$, —NR$_{2b}$R$_{2c}$, —SR$_{2d}$, —SO$_2$R$_{2e}$, —S(O)R$_{2f}$, or —P(O)OR$_{2g}$R$_{2h}$;

R$_3$ is hydrogen, halogen, cyano, nitro, alkyl, alkenyl, alkynyl, heteroalkyl, aryl, heteroaryl, heterocycle, cycloalkyl, cycloalkenyl, —OR$_{3a}$, —NR$_{3b}$R$_{3c}$, —SR$_{3d}$, —SO$_2$R$_{3e}$, —S(O)R$_{3f}$, or —P(O)OR$_{3g}$R$_{3h}$;

R$_4$ is hydrogen, halogen, cyano, nitro, alkyl, alkenyl, alkynyl, heteroalkyl, aryl, heteroaryl, heterocycle, cycloalkyl, cycloalkenyl, —OR$_{4a}$, —NR$_{4b}$R$_{4c}$, —SR$_{4d}$, —SO$_2$R$_{4e}$, —S(O)R$_{4f}$, or —P(O)OR$_{4g}$R$_{4h}$;

R$_5$ is hydrogen, halogen, cyano, nitro, alkyl, alkenyl, alkynyl, heteroalkyl, aryl, heteroaryl, heterocycle, cycloalkyl, cycloalkenyl, —OR$_{5a}$, —NR$_{5b}$R$_{5c}$, —SR$_{5d}$, —SO$_2$R$_{5e}$, —S(O)R$_{5f}$, or —P(O)OR$_{5g}$R$_{5h}$;

or R$_2$ and R$_3$ together with the atoms to which they are attached, R$_3$ and R$_4$ together with the atoms to which they are attached, or R$_4$ and R$_5$ together with the atoms to which they are attached, form a 5- or 6-membered saturated, partially unsaturated or fully unsaturated ring, the 5- or 6-membered ring optionally containing 1, 2 or 3 heteroatoms or heteroatom groups each independently selected from the group consisting of O, N, S, NO, SO and SO$_2$ as ring members, the 5- or 6-membered ring optionally fused to an aryl, heteroaryl, heterocycle, or cycloalkyl, the 5- or 6-membered ring substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl;

$R_{1a}$, $R_{1b}$, $R_{1c}$, $R_{2a}$, $R_{2b}$, $R_{2c}$, $R_{2d}$, $R_{2e}$, $R_{2f}$, $R_{2g}$, $R_{2h}$, $R_{3a}$, $R_{3b}$, $R_{3c}$, $R_{3d}$, $R_{3e}$, $R_{3f}$, $R_{3g}$, $R_{3h}$, $R_{4a}$, $R_{4b}$, $R_{4c}$, $R_{4d}$, $R_{4e}$, $R_{4f}$, $R_{4g}$, $R_{4h}$, $R_{5a}$, $R_{5b}$, $R_{5c}$, $R_{5d}$, $R_{5e}$, $R_{5f}$, $R_{5g}$, and $R_{5h}$, are each independently selected from the group consisting of hydrogen, alkyl, alkenyl, alkynyl, heteroalkyl, aryl, heteroaryl, heterocycle, cycloalkyl, and cycloalkenyl; and W$_1$ and W$_2$ are each independently selected from the group consisting of alkyl, alkenyl, alkynyl, alkoxy, heteroalkyl, aryl, heteroaryl, heterocycle, cycloalkyl, and cycloalkenyl; or W$_1$ and W$_2$ together with the carbon to which they are attached form a cycloalkyl, cycloalkenyl, or heterocycle;

wherein said alkyl, alkenyl, alkynyl, alkoxy, heteroalkyl, aryl, heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, the compound of formula (I') is not 2-(6-hydroxybenzo[d]thiazol-2-yl)-5,5-dimethyl-4,5-dihydrothiazole-4-carboxylic acid or 2-(6-aminobenzo[d]thiazol-2-yl)-5,5-dimethyl-4,5-dihydrothiazole-4-carboxylic acid. In certain embodiments, the compound of formula (I) is not 2-(6-hydroxybenzo[d]thiazol-2-yl)-5,5-dimethyl-4,5- dihydrothiazole-4-carboxylic acid or 2-(6-aminobenzo[d]thiazol-2-yl)-5,5-dimethyl-4,5-dihydrothiazole-4-carboxylic acid.

It is to be understood that any combination of $R_2$ and $R_3$ together with the atoms to which they are attached, $R_3$ and $R_4$ together with the atoms to which they are attached, and $R_4$ and $R_5$ together the atoms to which they are attached, can occur to form fused or unfused ring systems comprised of 5- or 6-membered rings.

In certain embodiments, $R_1$ is $-OR_{1a}$. In certain embodiments, $R_1$ is $-OR_{1a}$, wherein $R_{1a}$ is hydrogen or $C_1$-$C_4$-alkyl. In certain embodiments, $R_1$ is $-OH$.

In certain embodiments, $R_2$, $R_3$, $R_4$, and $R_5$, are each independently selected from the group consisting of hydrogen, halogen, cyano, nitro, $C_1$-$C_4$-alkyl, $C_2$-$C_4$-alkenyl, $C_2$-$C_4$-alkynyl, $-OH$, and $-NH_2$.

In certain embodiments, $R_4$ is $-OR_{4a}$, or $-NR_{4b}R_{4c}$. In certain embodiments, $R_4$ is $-OH$. In certain embodiments, $R_4$ is $-NR_{4b}R_{4c}$ where $R_{4b}$ and $R_{4c}$ are hydrogen. In certain embodiments, $R_4$ is $-NR_{4b}R_{4c}$ where $R_{4b}$ is hydrogen, and $R_{4c}$ is hydroxyalkyl.

In certain embodiments, $R_3$ and $R_4$ together with the atoms to which they are attached form a 5- or 6-membered optionally substituted saturated, partially unsaturated or fully unsaturated ring. In certain embodiments, $R_3$ and $R_4$ together with the atoms to which they are attached form a 5-membered optionally substituted heterocycle. In certain embodiments, $R_3$ and $R_4$ together with the atoms to which they are attached form a 6-membered optionally substituted heterocycle.

In certain embodiments, $R_4$ and $R_5$ together with the atoms to which they are attached form a 5- or 6-membered optionally substituted saturated, partially unsaturated or fully unsaturated ring. In certain embodiments, $R_4$ and $R_5$ together with the atoms to which they are attached form a 5-membered optionally substituted heterocycle. In certain embodiments, $R_4$ and $R_5$ together with the atoms to which they are attached form a 6-membered optionally substituted heterocycle. In certain embodiments, $R_4$ and $R_5$ together with the atoms to which they are attached form an optionally substituted aryl ring.

In certain embodiments, $R_3$ and $R_4$ together with the atoms to which they are attached form a 6-membered optionally substituted heterocycle, and $R_4$ and $R_5$ together with the atoms to which they are attached form a 6-membered optionally substituted heterocycle, wherein the two 6-membered rings are fused.

In certain embodiments, $W_1$ and $W_2$ are each alkyl. In certain embodiments, $W_1$ and $W_2$ are each $C_1$-$C_4$-alkyl. In certain embodiments, $W_1$ and $W_2$ together with the carbon to which they are attached form a cycloalkyl. In certain embodiments, $W_1$ and $W_2$ together with the carbon to which they are attached form a 3- to 8-membered cycloalkyl. In certain embodiments, $W_1$ and $W_2$ together with the carbon to which they are attached form a cycloalkenyl, such as a 5- to 8-membered cycloalkenyl. In certain embodiments, $W_1$ and $W_2$ together with the carbon to which they are attached form a heterocycle, such as a 5- to 8-membered heterocycle. The cycloalkyl, cycloalkenyl, or heterocycle group formed by $W_1$ and $W_2$ together with the carbon to which they are attached may be unsubstituted or substituted with one or more substituents, each independently selected from the group consisting of halogen, $=O$, $=S$, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, $-COOH$, ketone, amide, carbamate, silyl, substituted silyl, t-butyldimethylsilyl, alkylsulfanyl, sulfanyl, and acyl.

$G^1$ comprises a substrate of first enzyme, wherein biotransformation of the substrate by the first enzyme converts $G^1$ to H. In some embodiments, $G^1$ is $G^2$-$L^1$-; $G^2$ is the enzyme substrate and $L^1$ is a linker connecting $G^2$ to the remainder of the compound of formula (I') (i.e., the parent molecular moiety). $G^2$ is a group removable by the first enzyme.

In some embodiments, $L^1$ is a bond or a divalent group composed of an arrangement of atoms stable under neutral ambient conditions, the atoms being selected from carbon, hydrogen, nitrogen, oxygen, sulfur, phosphorus, and silicon. The divalent group may include single (e.g., $CH_2$—$CH_2$, $CH_2$—O), double (e.g., $C=O$), or triple bonds (e.g., CC), and may contain or include ring structures (e.g., a cycloalkyl). In some embodiments, the divalent group is an arrangement of one or more of $-C_{1-10}$alkylene-, $-C_{2-10}$alkylene-O—, $C_{3-8}$cycloalkylene, $-C(O)$—, $-O$—, $-S$—, $-S(O)$—, $-S(O)_2$—, $-NH$—, $-N(C_{1-4}$alkyl)-, $-N(COC_{1-4}$alkyl)-, an amino acid moiety, a protected amino acid moiety, and phenylene, wherein the $C_{3-8}$cycloalkylene and phenylene are optionally independently substituted with 1-4 substituents independently selected from the group consisting of $C_{1-4}$alkyl, $C_{1-4}$haloalkyl, $C_{1-4}$alkoxy, halo, cyano, or hydroxy. In some embodiments, $L^1$ is $C_1$-$C_{10}$alkylene (e.g., $C_2$-$C_3$alkylene).

$L^1$ may be a linker between a luciferin analogue and an enzyme substrate. In some embodiments, linker $L^1$ may be a traceless linker such as trimethyl lock, quinone methide, dipeptidyl, para-amino benzyloxycarbonyl, or alkylenediaminocarbonyl linkers as described in U.S. Ser. No. 62/541,350 (Encell et al., "COMPOSITIONS AND METHODS FOR STABILIZING BENZOTHIAZOLE LUCIFERIN ANALOGS," filed on Aug. 4, 2017) and shown below.

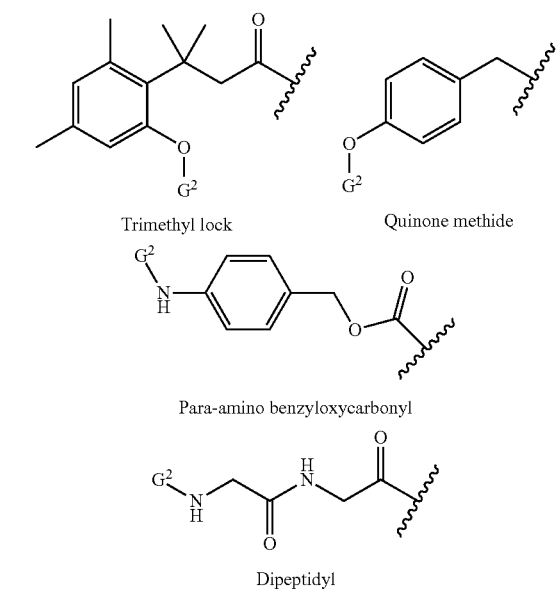

Trimethyl lock　　　Quinone methide

Para-amino benzyloxycarbonyl

Dipeptidyl

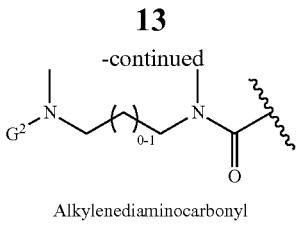

Alkylenediaminocarbonyl

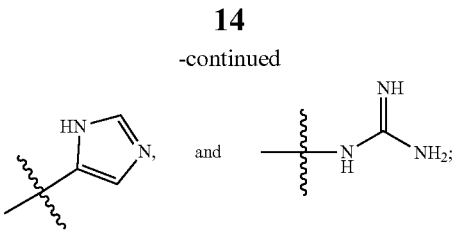

Enzymatic biotransformation of G² results in cleavage of the bond to the heteroatom to which G² is attached to release the linker that may spontaneously self immolate to release a benzothiazole luciferin analog. Some traceless linkers (e.g., alkylene linkers) may be spontaneously eliminated by β-elimination, as described in WO2006/130551.

Representative examples of an enzyme substrate G² include a substrate for a protease, a cytochrome (CYP) P450 reductase, a monoamine oxidase (MAO), a flavin monooxygenase (FMO), glutathione S transferase (GST), a dealkylase (e.g., demethylase), a deacetylase, a deformylase, a sulfatase, a phosphatase (e.g., alkaline phosphatase (AP)), a beta-lactamase, and alcohol dehydrogenase, as described in WO2006/130551 or US2007/0015790, which are incorporated herein by reference in their entireties.

Representative protease substrates include, but are not limited to, the peptides Z-DEVD-(SEQ ID NO: 1), Z-LETD-(SEQ ID NO: 2), GP-, Suc-LLVY-(SEQ ID NO: 3), Z-LRR-, Z-nLPnLD-(SEQ ID NO: 4), Z-QEVY-(SEQ ID NO: 5), VP-, Z-VDVAD-(SEQ ID NO: 6), Z-VEID-(SEQ ID NO: 7), Z-ATAD-(SEQ ID NO: 8), Z-IEPD-(SEQ ID NO: 9), Z-IETD-(SEQ ID NO: 10), Z-TSAVLQ-(SEQ ID NO: 11), and Z-VNSTLQ-(SEQ ID NO: 12) as described by Cosby et al. in Cell Notes (2007) 18, pp. 9-11, which is incorporated herein by reference in its entirety. In the case of these protease substrates, $L^1$ is a bond, as the enzyme substrate is directly attached to the luciferin analogue and is cleaved directly.

Other suitable linkers and $G^1$ moieties containing linkers includes those described in U.S. Ser. No. 62/541,350, which is incorporated herein by reference in its entirety.

In some embodiments, $R_1$ is $-NR_{1x}G^{10}$. The $-NR_{1x}G^{10}$ group is a group that is cleavable by a second enzyme to convert the $-NR_{1x}G^{10}$ group to $-OH$. As such, the $-CO-R_1$ moiety becomes a carboxy group ($-CO-OH$) following the cleavage of the $-NR_{1x}G^{10}$ group. In some embodiments, the $-NR_{1x}G^{10}$ group is

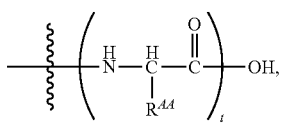

wherein $R^{AA}$ at each occurrence is independently hydrogen, alkyl, or alkyl substituted with a substituent selected from the group consisting of $-OH$, $-NH_2$, $-SH$, $-SCH_3$, phenyl, $-COOH$, $-CO-NH_2$,

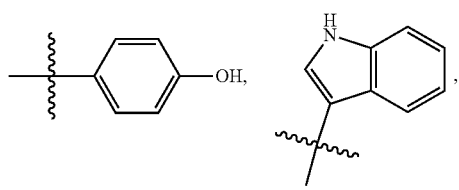

and t is 1-10. In some embodiments, t is 1, 2, 3, 4, or 5. In some embodiments, the $-NR_{1x}G^{10}$ group is

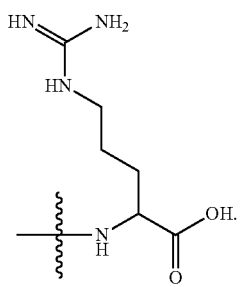 [SMILES: *NC(CCCNC(=N)N)C(=O)O]

The second enzyme catalyzes the cleavage of the $-NR_{1x}G^{10}$ group from the remainder of the compound, which converts to the $-NR_{1x}G^{10}$ group to $-OH$. In some embodiments, the second enzyme is a protease. In some embodiments, the second enzyme is a carboxypeptidase, such as carboxypeptidase B.

In some embodiments, the $-NR_{1x}G^{10}$ group is

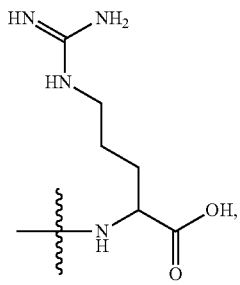

which can be cleaved from the remainder of the compound by carboxypeptidase B to convert the $-NR_{1x}G^{10}$ group to $-OH$. As such, the $-CO-R_1$ moiety of the compound becomes a carboxy group ($-CO-OH$) following the cleavage of the $-NR_{1x}G^{10}$ group, as shown below

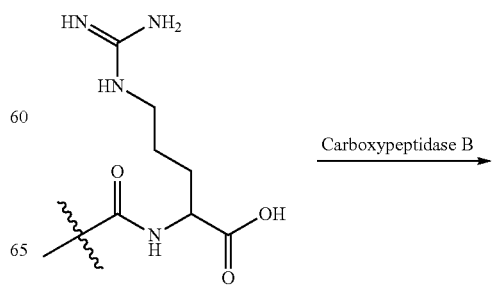

Carboxypeptidase B →

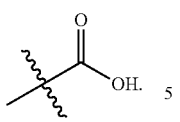

In certain embodiments, the compound of formula (I) has a structure of formula

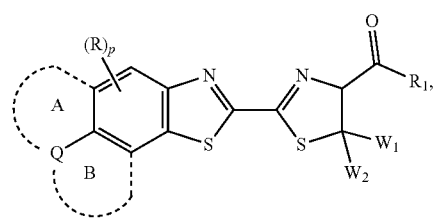

(I-a)

or a tautomer, or a salt thereof, wherein

A and B are each independently an optional 5- or 6-membered ring selected from the group consisting of aryl, heteroaryl, and heterocycle; wherein A, when present, is optionally substituted with one or more $R_A$; B, when present, is optionally substituted with one or more $R_B$; and each of $R_A$ and $R_B$, where present, is independently alkyl, halo, haloalkyl, hydroxyalkyl, —OH, —NH$_2$, or alkyl-NH—;

Q is —OR$_{Q1}$ or —NR$_{Q1}$R$_{Q1}$ when both A and B are absent, wherein R$_{Q1}$ at each occurrence is independently hydrogen, alkyl, or hydroxyalkyl; or Q is C, CR$_{Q2}$, CR$_{Q2}$R$_{Q2}$, N, NR$_{Q2}$, or O when at least one of A and B is present, wherein R$_Q$2 at each occurrence is independently hydrogen, alkyl, or hydroxyalkyl;

R is alkyl, alkoxy, halo, haloalkyl, hydroxyalkyl, hydroxy, cyano, nitro, amino, alkylamino, dialkylamino, alkenyl, alkynyl, heteroalkyl, aryl, heteroaryl, heterocycle, cycloalkyl, or cycloalkenyl; and p is 0, 1, 2, or 3;

wherein $R_1$, $W_1$, and $W_2$ are as defined above.

In certain embodiments, ring A is present and ring B is absent. In certain embodiments, ring A is absent and ring B is present. In certain embodiments, both ring A and ring B are present. In certain embodiments, both ring A and ring B are absent. In certain embodiments, both ring A and ring B are absent, and Q is —NHR$_{Q1}$.

In certain embodiments, the compound has a structure of formula (I-b) or (I-c):

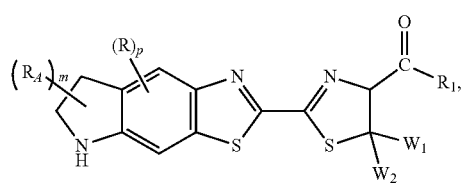

(I-b)

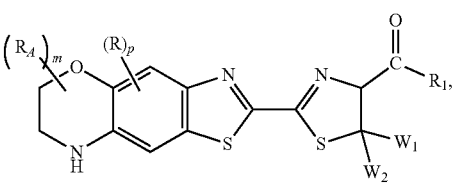

(I-c)

wherein m is 0, 1, 2, or 3; and p is 0, 1, or 2.

In certain embodiments, the compound has a structure of formula (I-d):

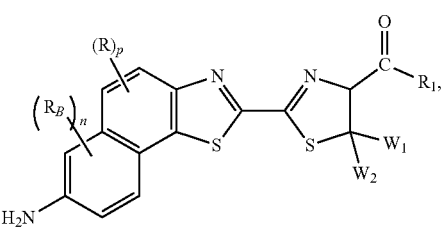

(I-d)

wherein n is 0, 1, 2, or 3; and p is 0, 1, or 2.

In certain embodiments, the compound has a structure of formula (I-e):

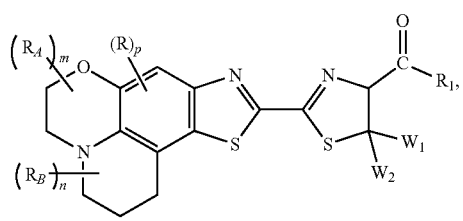

(I-e)

wherein m is 0, 1, 2, or 3; n is 0, 1, 2, or 3; and p is 0, or 1.

In certain embodiments, the compound has a structure of formula (I-f):

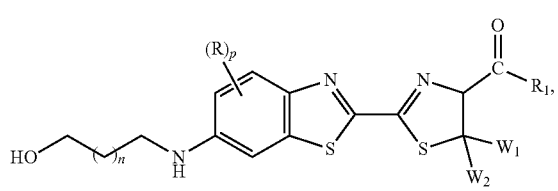

(I-f)

wherein p is 0, 1, 2, or 3; and n is 0, 1, 2, 3, 4, 5, 6, 7, or 8.

In certain embodiments, the compound has a structure of formula (I-g):

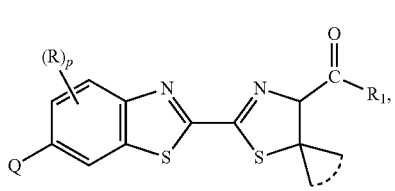

(I-g)

wherein
p is 0, 1, 2, or 3; and

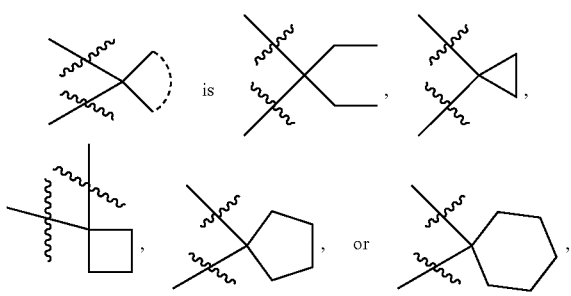

each of which is optionally substituted by as defined above for $W_1$ and $W_2$. In certain embodiments, $R_1$ is —OH. In certain embodiments, Q is —OH. In certain embodiments, $R_1$ is —OH, Q is —OH, and is

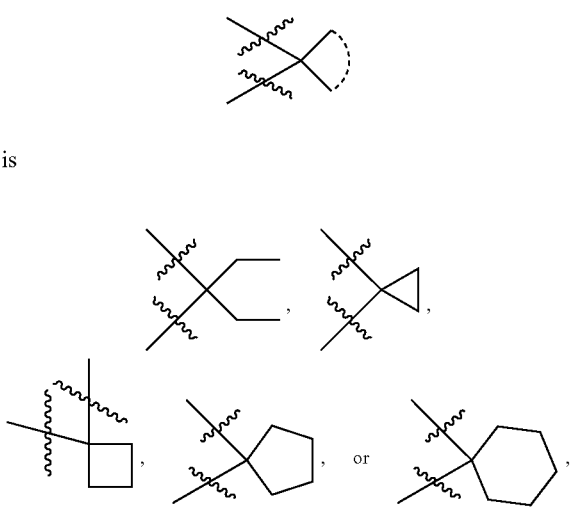

each of which is optionally substituted by as defined above for $W_1$ and $W_2$.

In some embodiments, disclosed are compounds of formula (I'), wherein $R_1$ is —OG$^1$, or —NR$_{1x}$G$^1$. In some embodiments, disclosed are compounds of formula (I'), wherein $R_2$ is —OG$^1$, or —NR$_{2x}$G$^1$. In some embodiments, disclosed are compounds of formula (I'), wherein $R_3$ is —OG$^1$, or —NR$_{3x}$G$^1$. In some embodiments, disclosed are compounds of formula (I'), wherein $R_4$ is —OG$^1$, or —NR$_{4x}$G$^1$. In some embodiments, disclosed are compounds of formula (I'), wherein $R_5$ is —OG$^1$, or —NR$_{5x}$G$^1$.

In some embodiments, disclosed are compounds of formula (I'), wherein $R_2$ and $R_3$ together with the atoms to which they are attached form a 5- or 6-membered saturated, partially unsaturated or fully unsaturated ring, the 5- or 6-membered ring substituted with a substituent selected from the group consisting of —OG$^1$, -NHG$^1$, and —N(C$_1$-C$_{10}$alkyl)G$^1$, the 5- or 6-membered ring further substituted with 0, 1, 2, or 3 other substituents as disclosed herein.

In some embodiments, disclosed are compounds of formula (I'), wherein $R_3$ and $R_4$ together with the atoms to which they are attached form a 5- or 6-membered saturated, partially unsaturated or fully unsaturated ring, the 5- or 6-membered ring substituted with a substituent selected from the group consisting of —OG$^1$, -NHG$^1$, and —N(C$_1$-C$_{10}$alkyl)G$^1$, the 5- or 6-membered ring further substituted with 0, 1, 2, or 3 other substituents as disclosed herein.

some embodiments, disclosed are compounds of formula (I'), wherein $R_4$ and $R_5$ together with the atoms to which they are attached form a 5- or 6-membered saturated, partially unsaturated or fully unsaturated ring, the 5- or 6-membered ring substituted with a substituent selected from the group consisting of —OG$^1$, -NHG$^1$, and —N(C$_1$-C$_{10}$alkyl)G$^1$, the 5- or 6-membered ring further substituted with 0, 1, 2, or 3 other substituents as disclosed herein.

In some embodiments, compounds of formula (I') contains a G$^1$ group and may be a substrate of a non-luciferase enzyme as disclosed herein. For example, the G$^1$ group of the compounds of formula (I') (such as the —OG$^1$, or —NHG$^1$ groups) may be subject to a biotransformation mediated by the non-luciferase enzyme to convert G$^1$ to H, which subsequently reveals a corresponding hydroxyl-luciferin analogue or amino-luciferin analogue. In some embodiments, the G$^1$ group may contain a linker between the moiety that serves as the substrate for the non-luciferase and the remaining structure of a luciferin analogue as disclosed herein. In some embodiments, G$^1$ is G$^2$-L$^1$-, wherein G$^2$ is a non-luciferase enzyme substrate and L$^1$ is a linker as described above. In some embodiments, G$^2$ is a group removable by a non-luciferase enzyme, and L$^1$ is a group that spontaneously hydrolyzes after the action of the non-luciferase enzyme. For example, the L$^1$ linker may be a traceless or self-immolating linker as described herein. Exemplary non-luciferase enzymes of interest, enzyme substrate moieties, and linkers include those described in WO2006/130551, which is incorporated herein by reference in their entireties.

In some embodiments, formula (I') is formula (II):

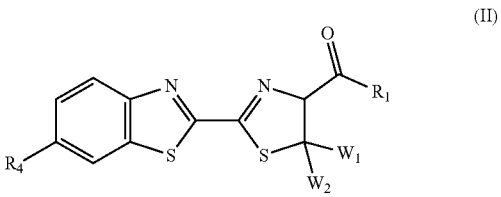

(II)

or a tautomer, or a salt thereof, wherein $R_4$ is —OG$^1$, -NHG$^1$, or —N(C$_1$-C$_{12}$alkyl)G$^1$; and $R_1$, $W_1$, and $W_2$ are as described above.

In some embodiments, disclosed are compounds of formula (II), wherein $R_4$ is —NH—CO-G$_2$. In some embodiments, formula (II) is formula (II-a):

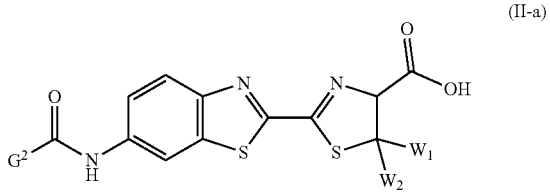

(II-a)

or a tautomer, or a salt thereof, wherein $G^2$, $W_1$, and $W_2$ are as described above.

In some embodiments, disclosed are compounds of formula (II-a), wherein $G^2$ is a peptide, such as those composed of natural amino acids. In some embodiments, $G^2$ is a peptide, which is a substrate for a non-luciferase enzyme of interest. For example, $G^2$ may be a peptide which includes the amino acids DEVD (SEQ ID NO: 13), and the non-luciferase enzyme of interest is Caspase 3, allowing this proluciferase substrate to report Caspase 3 activities in the presence of an appropriate luciferase.

Representative compounds of formula (I') or formula (I) include, but are not limited to:
5-(6-hydroxybenzo[d]thiazol-2-yl)-4-thia-6-azaspiro[2.4]hept-5-ene-7-carboxylic acid;
6-(6-hydroxybenzo[d]thiazol-2-yl)-5-thia-7-azaspiro[3.4]oct-6-ene-8-carboxylic acid;
2-(6-hydroxybenzo[d]thiazol-2-yl)-1-thia-3-azaspiro[4.4]non-2-ene-4-carboxylic acid;
2-(6-hydroxybenzo[d]thiazol-2-yl)-1-thia-3-azaspiro[4.5]dec-2-ene-4-carboxylic acid;
5,5-diethyl-2-(6-hydroxybenzo[d]thiazol-2-yl)-4,5-dihydrothiazole-4-carboxylic acid;
(S)-2-(5-fluoro-6-hydroxybenzo[d]thiazol-2-yl)-5,5-dimethyl-4,5-dihydrothiazole-4-carboxylic acid;
(R)-2-(5-fluoro-6-hydroxybenzo[d]thiazol-2-yl)-5,5-dimethyl-4,5-dihydrothiazole-4-carboxylic acid;
(S)-2-(7-aminonaphtho[2,1-d]thiazol-2-yl)-5,5-dimethyl-4,5-dihydrothiazole-4-carboxylic acid;
(S)-5,5-dimethyl-2-(6-(pyrrolidin-1-yl)benzo[d]thiazol-2-yl)-4,5-dihydrothiazole-4-carboxylic acid;
(S)-2-(6,7-dihydro-5H-thiazolo[4,5-f]indol-2-yl)-5,5-dimethyl-4,5-dihydrothiazole-4-carboxylic acid;
(S)-2-(6-((3-hydroxypropyl)amino)benzo[d]thiazol-2-yl)-5,5-dimethyl-4,5-dihydrothiazole-4-carboxylic acid;
2-(5-fluoro-6-hydroxybenzo[d]thiazol-2-yl)-1-thia-3-azaspiro[4.5]dec-2-ene-4-carboxylic acid;
5,5-dibenzyl-2-(6-hydroxybenzo[d]thiazol-2-yl)-4,5-dihydrothiazole-4-carboxylic acid;
5,5-diethyl-2-(5-fluoro-6-hydroxybenzo[d]thiazol-2-yl)-4,5-dihydrothiazole-4-carboxylic acid;
2-(6-hydroxybenzo[d]thiazol-2-yl)-1-thia-3-azaspiro[4.6]undec-2-ene-4-carboxylic acid;
2-(6-hydroxybenzo[d]thiazol-2-yl)-8-methyl-1-thia-3-azaspiro[4.5]dec-2-ene-4-carboxylic acid;
2-(6-hydroxybenzo[d]thiazol-2-yl)-8-methyl-1-thia-3,8-diazaspiro[4.5]dec-2-ene-4-carboxylic acid;
2-(6-hydroxybenzo[d]thiazol-2-yl)-5,5-dipropyl-4,5-dihydrothiazole-4-carboxylic acid; and
2-(6-hydroxybenzo[d]thiazol-2-yl)-8-oxa-1-thia-3-azaspiro[4.5]dec-2-ene-4-carboxylic acid,
or a tautomer, or a salt thereof.

Compound names are assigned by using Struct=Name naming algorithm as part of CHEMDRAW® ULTRA v. 12.0.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", 5$^{th}$ edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms as well as geometric isomers, and that these also constitute an aspect of the invention.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements, and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. a F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Properties of the Compounds (i) Thermal Stability

The disclosed compounds may exhibit superior thermal stability to known luciferins. Dehydroluciferin has been identified as a major product resulting from D-luciferin decomposition over time in solution (FIGS. 1 and 2). Dehydroluciferins can inhibit luciferases and lead to decreased light output, thus causing a significant impact on luciferase assays (FIG. 2).

Figure 3A:
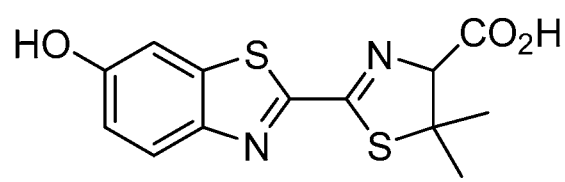
FIG. 3A shows the structures of 5,5-dimethyl luciferins III-a (6-OH compound) and III-b (6-$NH_2$ compound)
Figure 3A:
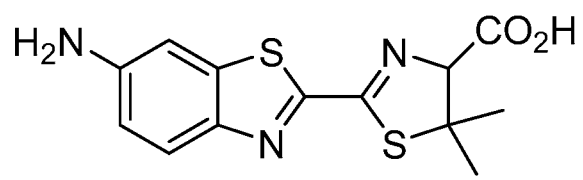
Figure 3B:
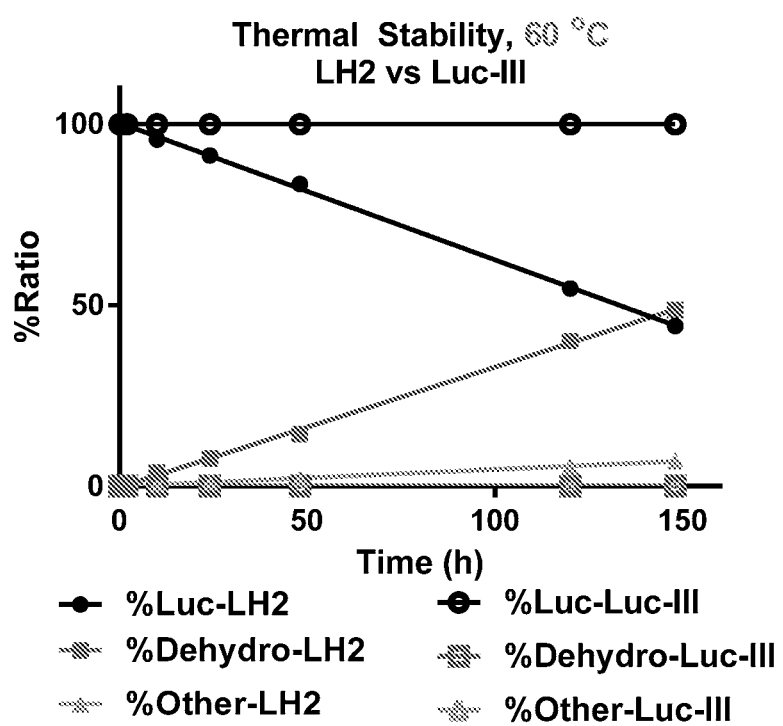
FIG. 3B shows the thermal stability of compound III-a or III-b as compared to luciferins.
Figure 4A:
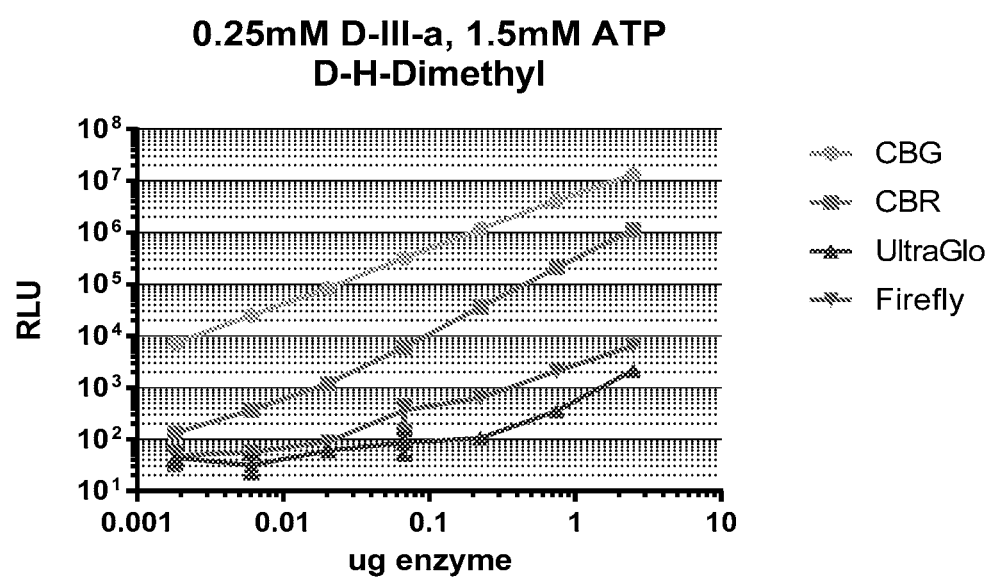
FIGS. 4A-4D show the results of luciferase assays using various luciferase enzymes.
Figure 4B:
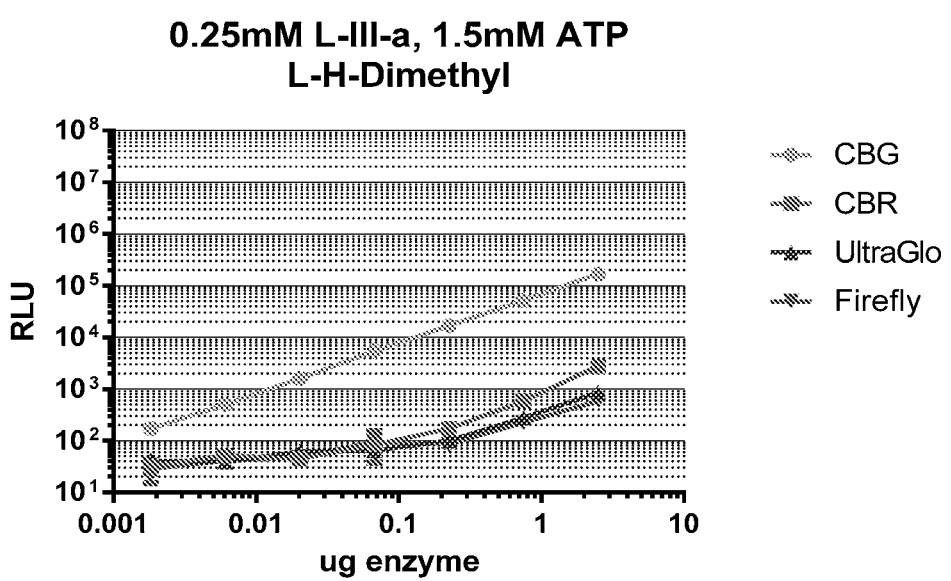
Figure 4C:
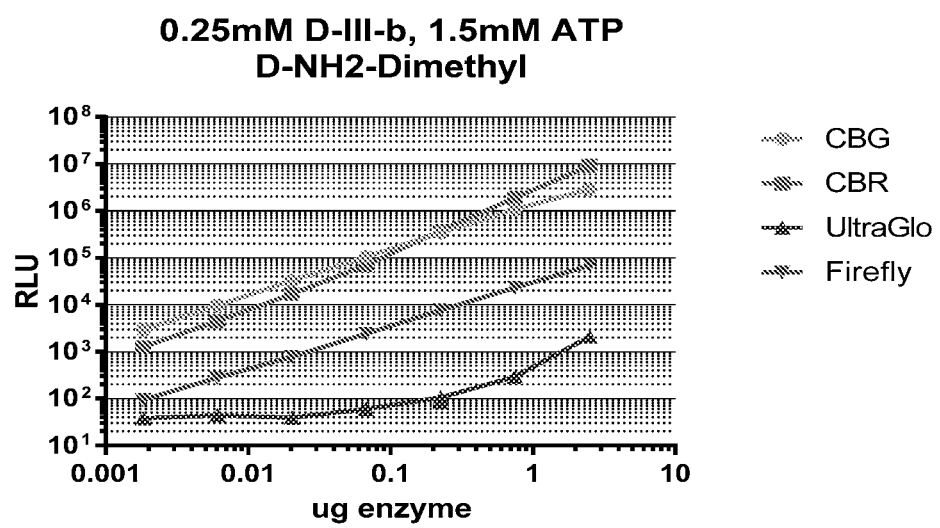
Figure 4D:
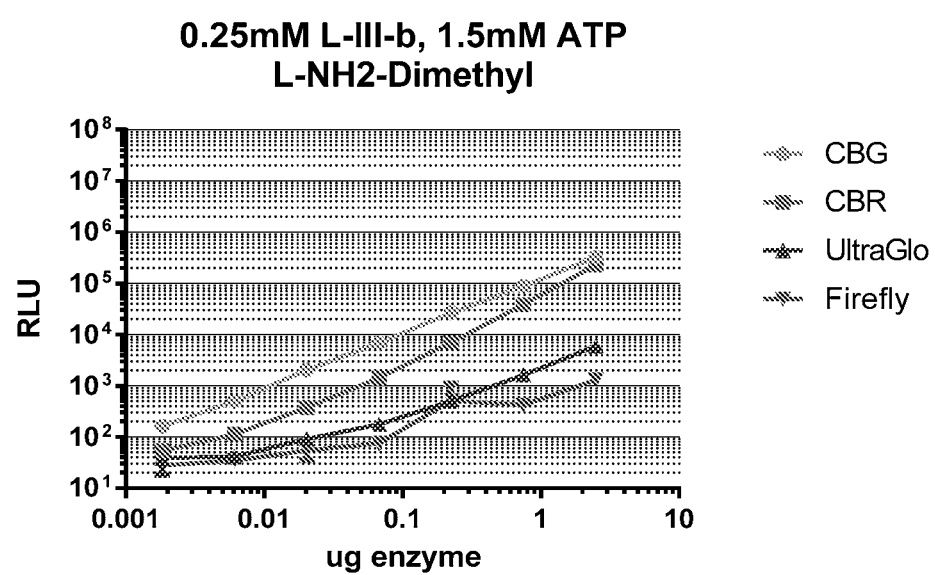
Figure 5A:
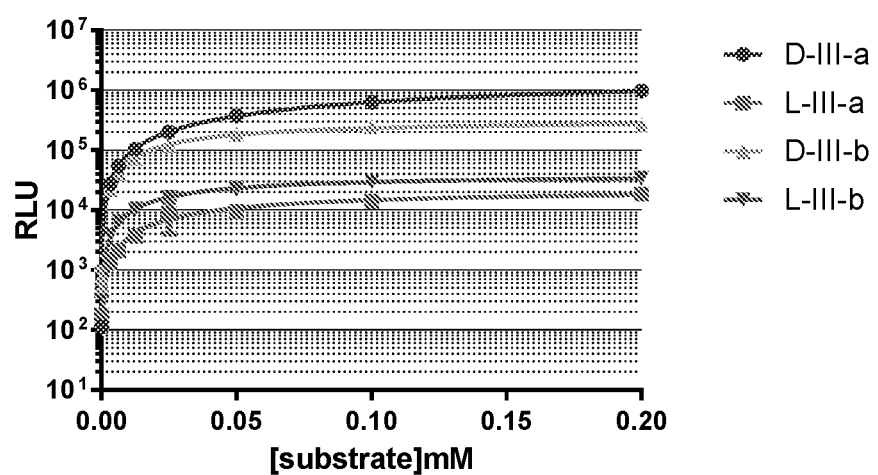
FIGS. 5A-5F show the results of luciferase assays at various substrate concentrations.
Figure 5B:
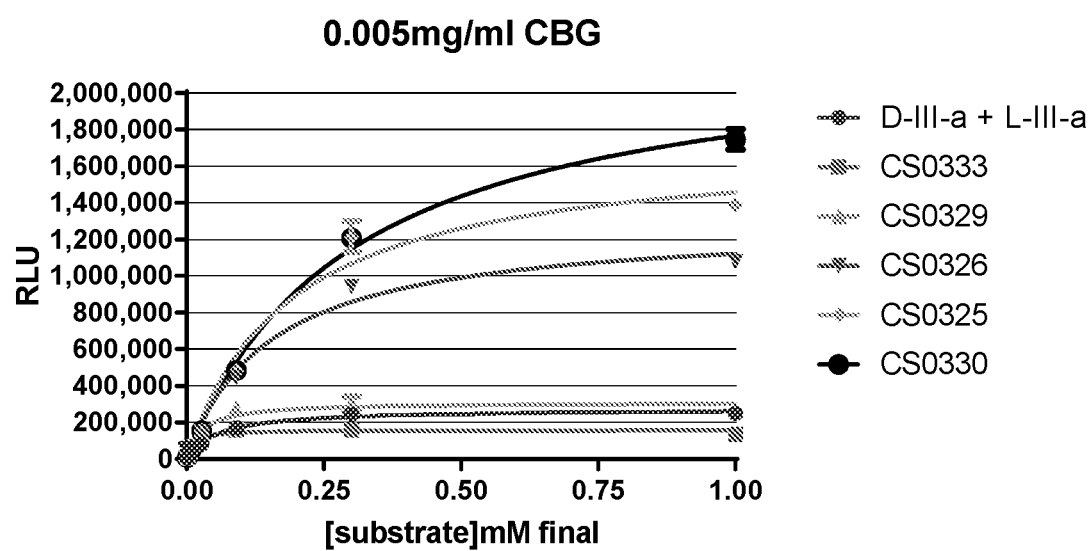
Figure 5C:
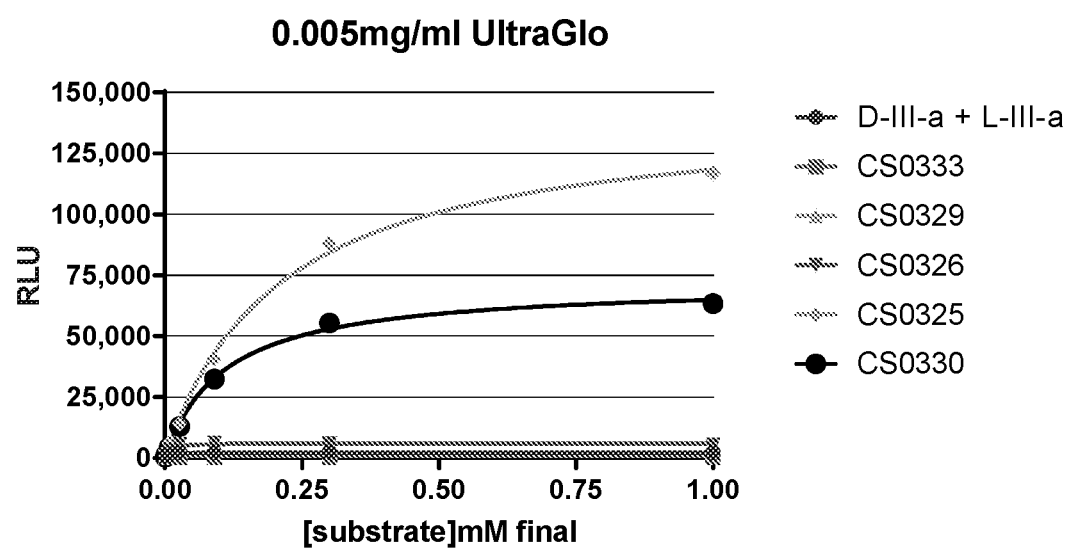
Figure 5D:
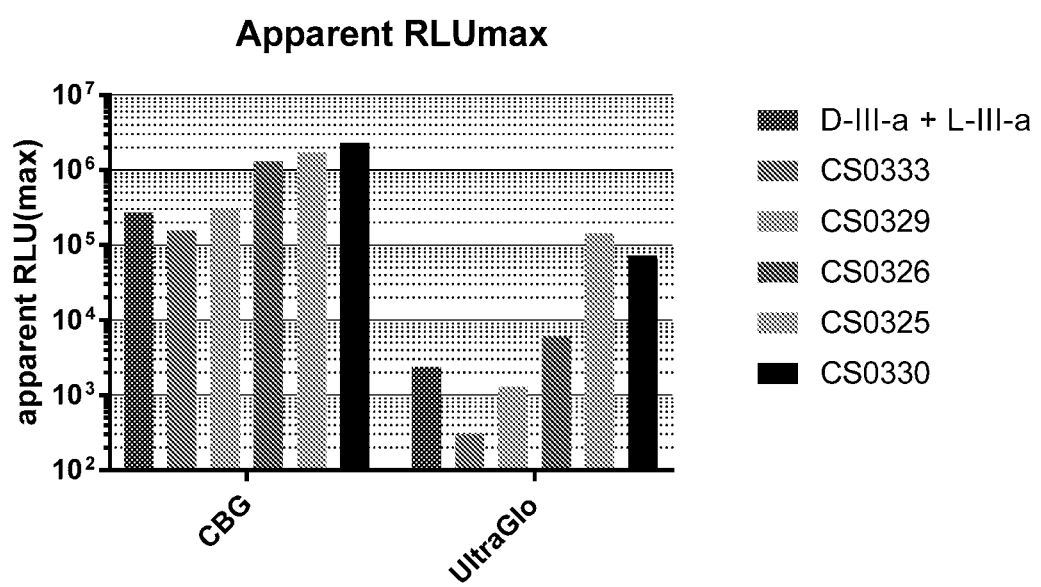
Figure 5E:
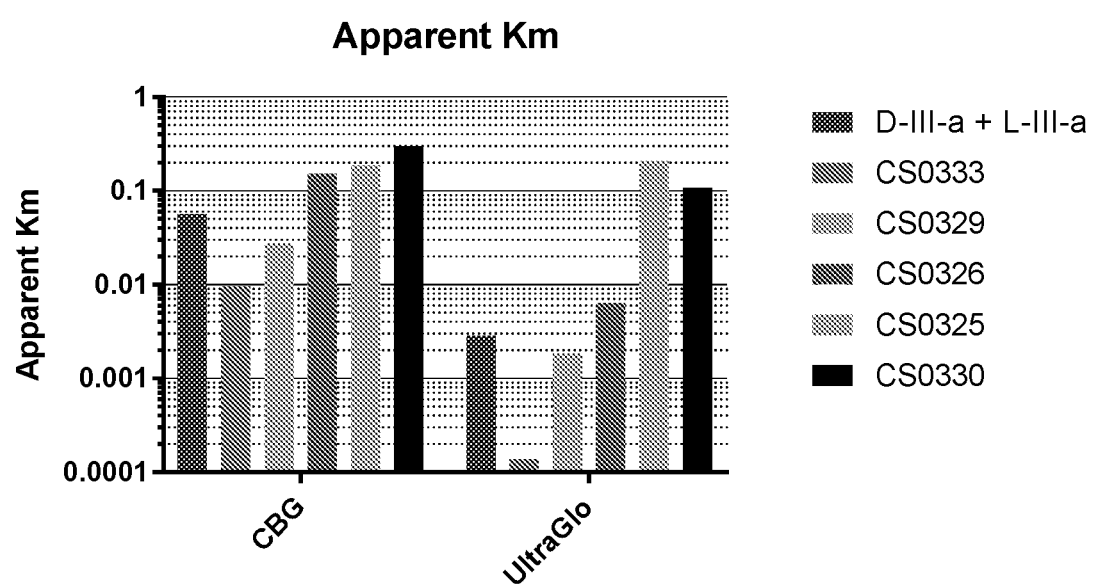
Figure 5F:
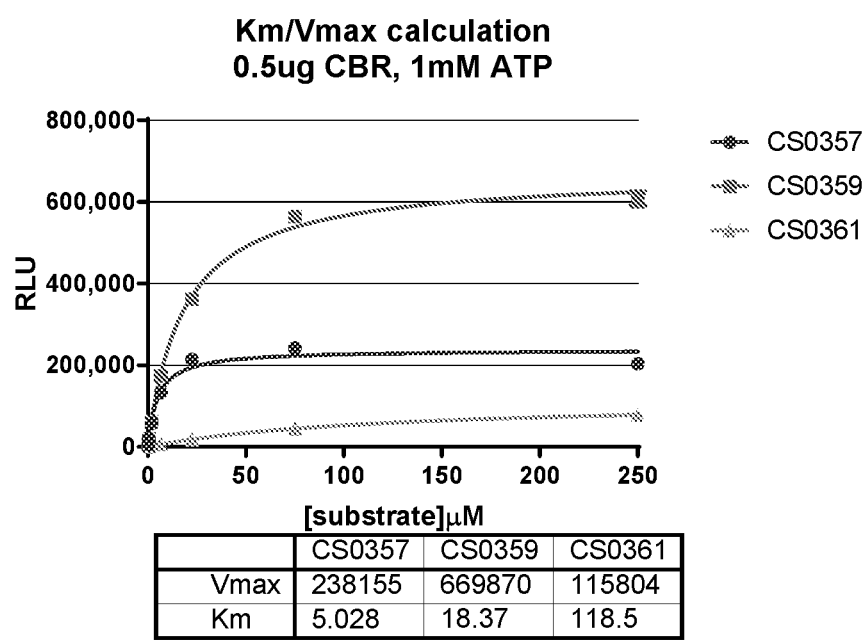

The disclosed 5,5-disubstituted luciferin analogues may exhibit improved thermal stability in solution (FIG. 3). As shown in FIG. 3B, virtually no decomposition occurred in the 5,5-dimethyl luciferins III-a (6-OH compound) and III-b (6-NH$_2$ compound), while significant decomposition is observed in the unsubstituted luciferin with corresponding production of dehydroluciferin. The 5,5-disubstitution may improve the overall thermal stability of luciferin analogue compounds by eliminating the possibility of dehydroluciferin formation.

As used herein, "thermal stability" may refer to how stable a luciferin analogue compound is in a solution over a certain time period such that it maintains the ability to produce light in the presence of a luciferase, including, for example, live cell assays using a live cell luciferase. The solution of the luciferin analogue may include a liquid media in which a luciferase is present, such as an aqueous buffer system in which a luciferase assay is conducted. Stability for the disclosed compounds may be demonstrated by the percentage of degradation of the compounds in a specific environment over time. The percentage of purity for a particular compound can be determined by a variety of techniques known to those skilled in the art. These techniques include, for example, nuclear magnetic resonance (NMR) and high performance liquid chromatography (HPLC).

In some embodiments, the thermal stability of the disclosed compounds may be determined after a solution of a particular compound has been stored, in the absence or presence of a luciferase, at a certain temperature over a certain period of time. The temperature during the storage may be 20° C. or higher, 30° C. or higher, 40° C. or higher, 50° C. or higher, 60° C. or higher, or 70° C. or higher. In some embodiments, the disclosed compounds are combined with a luciferase (or a biological sample containing a luciferase) in a solution, which is kept at a temperature (such as 20-70° C.) for a certain period of time.

In some embodiments, the present compounds can provide a stable luminescence signal in a solution at ambient or elevated temperature (such as 30-70° C.) for a period of at least 24 hours, at least 48 hours, at least 60 hours, at least 80 hours, at least 100 hours, at least 120 hours, at least 150 hours, at least 200 hours, at least 250 hours, at least 300 hours, at least 350 hours, or at least 400 hours. In some embodiments, the present compounds can provide a stable luminescence signal in a luciferase assay medium at ambient temperature for a period of 100-400 hours. The disclosed compounds having improved thermal stabilities in solution may allow for applications that require long term storage of luciferins in solutions over time at ambient temperature. The disclosed compounds may be particularly useful for applications where formation of dehydroluciferin is significant and detrimental, such as Reactive Oxygen Species (ROS) detection or P450 assays.

The present compounds demonstrate superior thermal stability as compared to luciferin analogues lacking 5,5-disubstitution over the same period of time. In some embodiments, the present compounds show an improved thermal stability of at least 10%, at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, at least 450%, or at least 500% as compared to luciferin analogues lacking 5,5-disubstitution. The remarkable stability of the present compounds allows for longer storage without decomposition of the luciferin analogues, which may be used for a variety of enhancements of luminogenic assays.

In some embodiments, the thermal stability of the present compounds may be enhanced by storing them in solution with additives. These additives may enhance the stability of the present compounds by preventing oxidative decomposition or other forms of decomposition. The stability enhancement may be through scavenging of reactive oxygen species such as oxygen or hydrogen peroxide, by converting oxidized compounds back to the original compound through reduction, or by another mechanism. In some embodiments, these additives are compatible with the reaction of the present compounds with a luciferase, causing no decrease in light production. In some embodiments, these additives are Azathiothymidine (ATT) or analogs thereof, as described in U.S. Ser. No. 62/541,350, which is incorporated by reference herein in its entirety. In some embodiments, the additive is thiourea or another carbon-sulfur double bond containing compound.

(ii) Light Production

The disclosed compounds, surprisingly, may produce sufficient light to be suitable substrates for luciferase assays using various luciferases. In some embodiments, the disclosed compounds provide much stronger light signal than the 5,5-dimethyl luciferins in luciferase assays under various conditions. For example, both firefly luciferases and click beetle luciferases can effectively utilize various stereoisomeric forms (e.g., both D- and L-forms in mixture) of the disclosed 5,5-disubstituted luciferin analogues to produce bioluminescence over a broad range of pH (FIGS. 4A-6B). It was unclear from the previous studies whether any particular 5,5-disubstituted luciferin analogues would produce sufficient light to be useful in luciferase assays. Further, 5,5-disubstituted luciferins were previously believed to produce light only via chemiluminescent processes, not via enzymatic processes by firefly luciferases. For example, compound III-a was considered incapable of producing light via firefly or click beetle luciferases mediated processes (Branchini et al., *J. Am. Chem. Soc.* 2002, 124, 2112-2113). Only the D-form of Compound III-b, on the other hand, was shown to produce light when tested with recombinant beetle luciferases (Viviani et al., *Biochemistry*, 2014, 53, 5208-5220). The reduced activity of 5,5-dimethylluciferin substrate as compared to luciferin appears to suggest that, to some extent, any substrate having more steric bulk at the 5-position of the luciferin structure would result in poor activities for luciferase assays. However, the disclosed compounds surprisingly demonstate that the steric hindrance imparted by the substituent at the 5-position would not necessarily reduce the substrate's activity. In certain embodiments, the disclosed compounds having larger substituent groups than the 5,5-dimethyl compounds (for example, the 5,5-diethyl or cyclohexyl substrates) show higher luciferase activities than the 5,5-dimethyl compounds, contrary to the expectation that higher steric hindrance would reduce activity. Thus, due to their unprecedented activities in luciferase assays, the disclosed compounds provide unexpected advantage over the known 5,5-disubstituted luciferins.

"Luminescence" refers to the light output of a luciferase under appropriate conditions, e.g., in the presence of a suitable substrate such as a luciferin analogue. The light output may be measured as an instantaneous or near-instantaneous measure of light output (which is sometimes referred to as "T=0" luminescence or "flash") at the start of the luminescence reaction, which may be initiated upon addition of the luciferin substrate. The luminescence reaction in various embodiments is carried out in a solution. In other embodiments, the luminescence reaction is carried out on a solid support. The solution may contain a lysate, for example from the cells in a prokaryotic or eukaryotic expression system. In other embodiments, expression occurs in a cell-free system, or the luciferase protein is secreted into an extracellular medium, such that, in the latter case, it is not necessary to produce a lysate. In some embodiments, the reaction is started by injecting appropriate materials, e.g., luciferin analogue, buffer, etc., into a reaction chamber (e.g., a well of a multiwell plate such as a 96-well plate) containing the luminescent protein. In still other embodiments, the luciferase and/or luciferin analogues (e.g., compounds of formula (I)) are introduced into a host, and measurements of luminescence are made on the host or a portion thereof, which can include a whole organism or cells, tissues, explants, or extracts thereof. The reaction chamber may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

Compounds of formula (I) can be used in bioluminescent assays to provide RLUs of greater than or equal to 1, greater than or equal to 2, greater than or equal to 3, greater than or equal to 4, greater than or equal to 5, greater than or equal to 10, greater than or equal to 20, greater than or equal to 30, greater than or equal to 40, greater than or equal to 50, or greater than or equal to 100, relative to luciferin or a known luciferin analogues.

B. Synthesis Methods

Compounds of formula (I) can be synthesized as shown in Scheme 1. Abbreviations which have been used in the descriptions of the Schemes that follow are: DMF for dimethylformamide.

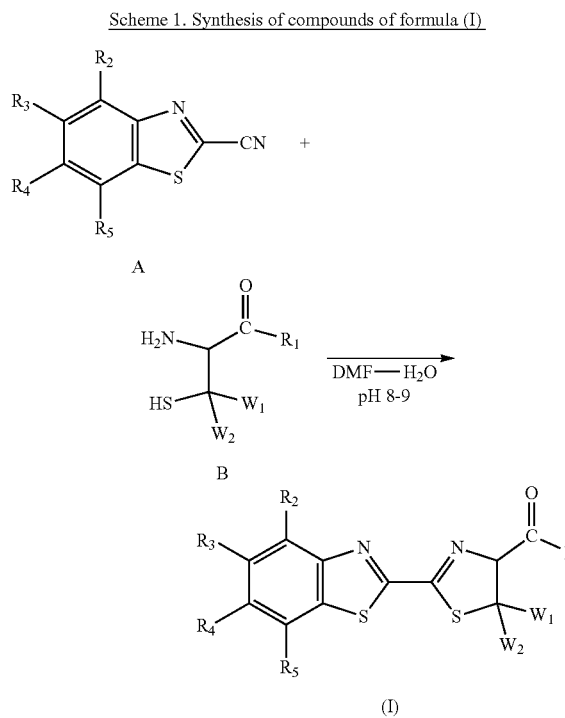

As shown in Scheme 1, compounds of formula (I) can be prepared by treating a benzo[d]thiazol-2-yl intermediate A with the β,β-disubstituted cysteine derivatives. The reaction can be conducted in a solution of dimethylformamide and water at a pH of 8-9.

Optimum reaction conditions and reaction times for each individual step can vary depending on the particular reactants employed and substituents present in the reactants used. Specific procedures are provided in the Examples section. Reactions can be worked up in the conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

3. METHODS OF USE AND KITS

The present luciferin analogues may serve as substrates in enzyme activity assays or non-enzymatic biological assays, e.g., reporter gene assays, for a desired enzyme. In some embodiments, the desired enzyme may be a nonluciferase, and the present luciferin analogues may be used as a substrate of the nonluciferase enzyme and as a prosubstrate for luciferase. In other embodiments, the present luciferin analogues may be modified by a molecule of interest, which modified molecule is a substrate for luciferin. Surprisingly, the present luciferin analogues can have activity as substrates for luciferase in a light generating assay. Thus, numerous nonluciferase enzymes or luciferase enzymes may be measured in a bioluminescent assay using the present luciferin analogues.

The compounds of the disclosure may be used in any way that luciferase substrates, e.g., luciferin analogues, have been used. For example, they may be used in a bioluminogenic method that employs an analogue of luciferin to detect one or more molecules, e.g., an enzyme, a cofactor for an enzymatic reaction, an enzyme substrate, an enzyme inhibitor, an enzyme activator, or OH radicals, or one or more conditions, e.g., redox conditions, in a sample. The sample may include an animal (e.g., a vertebrate), a plant, a fungus, physiological fluid (e.g., blood, plasma, urine, mucous secretions), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution, including multiphasic solutions (e.g., emulsions or suspensions), or on solid supports (e.g., particles, capillaries, or assay vessels).

In certain embodiments, the compounds of formula (I') or formula (I) may be used to quantify molecules of interest. In some embodiments, compounds of formula (I') or formula (I) can be used as a probes of a specific biochemical activity, e.g., apoptosis or drug metabolism. In some embodiments, the compounds of formula (I') or formula (I) can be coupled to a specific enzyme activity, wherein the compound can be acted on by the specific enzyme of interest. In some embodiments, the approach can be used for enzymes such as those used in drug metabolism, e.g., cytochrome P450 enzymes, monoamine oxidase, and glutathione S-transferase; and apoptosis, e.g., caspases. In some embodiments, the luciferin analogues may be combined with other components necessary to support luminescence, e.g., a luminescent protein such as a luciferase, to provide a single reagent and a homogeneous assay. For example, luminescence may be generated when a luciferin analogue and a luciferase are added to a sample.

The methods may be used, for example, to determine the presence or amount of at least one molecule, e.g., a nonluciferase enzyme, a regulator of a nonluciferase enzyme, a nonluciferase enzyme substrate, and/or cofactors of the reaction, or a condition in a sample. In certain embodiments, the disclosed methods provide a rapid method for detecting one or more molecules in a single sample such as an aliquot of cells or a lysate thereof. In certain embodiments, the method includes quantifying the presence, amount or specific activity of a molecule such as an enzyme, substrate or cofactor in a bioluminogenic assay or quantifying the presence or amount of an enzyme, substrate or cofactor in a fluorogenic assay. The intensity of the bioluminogenic or fluorogenic signal is a function of the presence or amount of the respective molecule. In addition, the reaction may contain one or more test agents, e.g., enzyme inhibitors or activators, and/or different concentrations of inhibitors or activators. In certain embodiments, the method employs at least two different reactions, where the first reaction is a nonluciferase enzyme-mediated reaction and the second reaction is a beetle luciferase-mediated reaction. In another embodiment, the first reaction is a nonenzymatic reaction and the second reaction is a beetle luciferase-mediated reaction. In yet another embodiment, the method employs a single reaction, e.g., a beetle luciferase-mediated reaction or a fluorogenic reaction.

Thus, a bioluminogenic assay may directly or indirectly detect, e.g., measure, the amount, presence or specific activity of, for example, a cofactor for an enzyme-mediated reaction, an enzyme, an enzyme substrate, an inhibitor of the enzyme, an activator of the enzyme, or a condition. For instance, in certain embodiments, a beetle luciferase and a luciferin analogue that is a substrate of the beetle luciferase may be employed in a bioluminogenic assay to detect ATP concentration. In another embodiment, a luciferin analogue which is a substrate for a nonluciferase enzyme, for instance, a derivative which is a substrate of a monoamine oxidase, yields a product which is a substrate for a beetle luciferase, and so may be employed in a bioluminogenic assay to detect the oxidase. In certain embodiments, the luciferin analogue is a prosubstrate of a beetle luciferase, which yields a product that is a substrate of luciferase but does not itself yield a substantial amount of light in a reaction with the beetle luciferase. In some embodiments, the analogue is a substrate for a nonluciferase enzyme or useful to detect another molecule, and a substrate for luciferase which yields a substantial amount of light. In this embodiment, the analogue is altered by luciferase but is generally inefficient in a light generating reaction. In some embodiments, the luciferase and substrate of the luciferase, e.g., luciferin, luciferin derivative, functional analog, or novel luciferin derivative capable of generating light when the luciferase substrate, e.g., luciferin derivative disclosed herein, have enhanced stability to the conditions of the assay and/or the lysis reagents, e.g., assay stability, storage stability for individual chemical components in isolation or as a contained, multicomponent mixed liquid solution.

In certain embodiments, disclosed is a bioluminescent assay method to detect one or more nonluciferase enzymes. The method includes contacting a sample suspected of having one or more nonluciferase enzymes, or a substrate or a co-factor for the nonluciferase-mediated reaction, with a corresponding reaction mixture that includes a luciferin analogue that is a substrate for the nonluciferase enzyme. In certain embodiments, the analogue is one having a modification in the G1 ring of D-luciferin (FIG. 1) that includes a recognition site for the nonluciferase enzyme, e.g., for a phosphatase. In another embodiment, the analogue is one having a modification in the G2 ring of D-luciferin which analogue is a substrate for luciferase or a prosubstrate for luciferase. In another embodiment, the derivative is one having a modification in the G3 ring of luciferin that includes a recognition site for an enzyme of interest, e.g., acetylcholinesterase. In another embodiment, the derivative is one having a modification in one of the rings that includes a recognition site for the enzyme of interest, as well as a further modification in that ring or one or more of the other rings.

For analogues that are a substrate for luciferase, as well as optionally a substrate of a nonluciferase enzyme or other molecules, the analogues may be employed to detect luciferase, or a co-factor, inhibitor, or activator of the luciferase reaction. If the analogue is a prosubstrate for luciferase, i.e., the product of a reaction between the analogue and the nonluciferase enzyme is a substrate for luciferase, sequential or concurrent reactions for the nonluciferase enzyme and the luciferase may be conducted. For instance, a reaction for a nonluciferase enzyme that contains the prosubstrate may be conducted in a single well and a beetle luciferase reaction mixture added to that well. In another embodiment, a reaction mixture for a nonluciferase enzyme that contains the prosubstrate is conducted in a single well and a portion of that reaction added to a different well having a beetle luciferase reaction mixture. Alternatively, reactions may be conducted simultaneously in the same well.

The disclosure thus provides a method to detect or determine the presence or amount of a molecule for a nonluciferase enzyme-mediated reaction in a sample. The method includes contacting a sample, a first reaction mixture for a nonluciferase enzyme-mediated reaction, and a luciferin analogue (such as compounds of formula (I') or formula (I)) which is a substrate for the nonluciferase enzyme, so as to yield a first mixture or providing such a first mixture comprising a luminogenic product that is a substrate for a luciferase, or providing such a first mixture. At least a portion of the first mixture is contacted with a second reaction mixture for a beetle luciferase-mediated reaction, so as to yield a second mixture. Then, luminescence in the second mixture is detected or determined, thereby detecting or determining the presence or amount of a molecule for the nonluciferase enzyme-mediated reaction in the sample. In some embodiments, the nonluciferase reaction mixture or luciferase reaction mixture may include an esterase, e.g., if the product of the reaction between the analogue and the nonluciferase enzyme has an ester group and that product is a proluciferase substrate. The esterase may be included with the first reaction mixture, added prior to initiation of the luciferase reaction mixture, or included in the luciferase reaction mixture. In some embodiments, e.g., an analogue with a picolinyl ester, the product of the reaction between the analogue and the nonluciferase enzyme is a substrate for luciferase in the absence of an exogenously added esterase. In certain embodiments, luciferin analogues having an ester modification are employed in methods of the disclosure, such as those to detect nonluciferase enzymes including cytochrome P450 enzymes, as those analogues may have improved properties as a nonluciferase substrate. Although not intending to be bound by any mechanism, the inclusion of the ester modification at position 4 in the G3 ring may block negative charges or add a lipophilic quality to the derivative, rendering it an improved substrate.

Further provided is a method to detect or determine the presence or amount of a molecule for a nonluciferase enzyme-mediated reaction in a sample. The method includes contacting a sample, a reaction mixture for a nonluciferase-mediated enzyme reaction and for a luciferase-mediated reaction, and a luciferin analogue which is a substrate for the nonluciferase enzyme, yielding a mixture. A reaction between the nonluciferase enzyme and the present luciferin analogues yields a luminogenic product that is a substrate for the luciferase. Luminescence in the mixture is detected or determined, thereby detecting or determining the presence or amount of a molecule for the nonluciferase-mediated reaction in the sample.

The disclosure further provides a method to detect or determine the presence or amount of a molecule for a luciferase-mediated reaction in a sample. The method includes contacting a sample, a reaction mixture for a beetle luciferase, and a luciferin analogue which is a substrate for the luciferase, to yield a reaction.

The disclosure also provides a method to detect the presence or amount of a molecule in a sample. The method includes contacting a sample, a first reaction mixture for a nonenzyme-mediated reaction and a luciferin analogue which in the presence of the molecule yields a luminogenic product that is a substrate for a luciferase, and then contacting at least a portion of the first reaction and a second reaction mixture for a luciferase-mediated reaction, to yield a second reaction. Luminescence in the second reaction is detected or determined, thereby detecting or determining the presence or amount of the molecule. For instance, a mixture is provided having a sample, a first reaction mixture for a nonenzyme-mediated reaction and a luciferin analogue which in the presence of the molecule yields a luminogenic product that is a substrate for a beetle luciferase. At least a portion of the first mixture and a second reaction mixture for a beetle luciferase-mediated reaction are mixed, to yield a second mixture, and then luminescence in the second mixture is detected or determined, thereby detecting or determining the presence or amount of the molecule.

For the biolumingenic assays described herein which employ luciferin analogues with a lower background, those assays can use lower (or higher) amounts of the analogue, and those analogues may have improved reactivity, e.g., with a nonluciferase enzyme. In addition, for any of the bioluminogenic assays described herein, other reagents may be added to reaction mixtures, including but not limited to those that inhibit or prevent inactivation of luciferase, or otherwise extend or enhance luminescent signal.

Also provided is a method to identify or measure the potency of a modulator of a nonluciferase enzyme-mediated reaction. The method includes contacting one or more agents, a first reaction mixture for a nonluciferase enzyme-mediated reaction, and a luciferin analogue which is a substrate for the nonluciferase enzyme, so as to yield a first mixture, or providing such a mixture, wherein the analogue includes a G1 or G2 ring modification relative to D-luciferin. The first mixture in the absence of the one or more agents includes a luminogenic product that is a substrate for a beetle luciferase. At least a portion of the first mixture and a second reaction mixture for a beetle luciferase-mediated reaction are mixed, so as to yield a second mixture. Luminescence in the second mixture is compared with a control mixture, thereby identifying whether one or more of the agents modulates the nonluciferase enzyme-mediated reaction and/or to what extent and with what potency.

In certain embodiments, test compounds can be screened and evaluated for their activities as substrates or cofactors of, or regulators, either inhibitors or activators, of an enzymatic or nonenzymatic reaction by using the luciferin and fluorophore analogue of the present invention. A candidate compound may be determined to be regulator or a substrate of a reaction by contacting a reaction mixture with an analogue and the test compound, under conditions that would, in the absence of the test compound, yield bioluminescence, fluorescence, or a bioluminogenic product.

In one aspect, a method is provided to distinguish between a substrate and an inhibitor of a reaction. For example, the compound is incubated with at least one enzyme under conditions which allow for metabolism of the compound prior to providing a luciferin analogue under conditions that, in the absence of an inhibitor or substrate of the enzyme, would be suitable for interaction between the luciferin analogue and the enzyme. In certain embodiments, the product of that reaction is a substrate of luciferase and in the presence of luciferase yields a light emitting second reaction. The resulting light emitting reaction is compared to the one obtained from contacting the enzyme with the compound and the analogue, under conditions that would, in the absence of an inhibitor of the enzyme, be suitable for interaction between the luciferin analogue and the enzyme. Metabolism of the compound by the enzyme reduces its concentration in the assay medium and may lead to an apparent loss of inhibitory activity compared to conditions without metabolism of the compound which would indicate it was a substrate for the enzyme. An inhibitory compound that was not metabolized would show equal potency, irrespective of the time of addition of the substrate.

In one aspect, the compound is preferably contacted first with the enzyme for a first predetermined time period. Thereafter, the mixture is contacted with a luciferin analogue and bioluminescent enzyme, e.g., luciferase, simultaneously or contemporaneously, and the mixture is allowed to incubate for a second predetermined time period.

In another aspect, the compound is incubated with the enzyme for a first predetermined time period to form a first mixture. Thereafter, the first mixture is contacted with the luciferin analogue, to form a second mixture that is allowed to incubate for a second predetermined time period. The second mixture is then contacted with a bioluminescent enzyme, e.g., luciferase, to form a third mixture, which is allowed to incubate for a third predetermined time period. Thereafter, the activity resulting from the interaction of the enzyme with the compound is determined by measuring luminescence during and/or after the third predetermined time period relative to a control (e.g., no compound) reaction. In this way, for example, mechanism based inhibitors of the first enzyme can be identified and distinguished from nonmechanism based inhibitors because the first incubation with the test compound but without the luciferin analogue will lead to a more profound inhibition by a mechanism based inhibitor than would be observed without the first incubation or substrates of the first reaction will show reduced inhibition.

In another aspect, a cell-based method is provided for screening a compound to determine its effect on enzyme activity of the cell. The test compound is contacted with a cell having the enzyme, either naturally or via recombinant expression, the luciferin analogue, and bioluminescent enzyme, e.g., luciferase, or contacted with a cell having the enzyme and luciferase, and the analogue, for a predetermined period of time. Thus, in certain embodiments, a cell that either transiently or stably expresses a recombinant enzyme such as a bioluminescent enzyme, e.g., luciferase, may be employed. Any conventional method for creating transient or stable transfected cells may be used. In certain embodiments, a luciferin analogue is contacted with and diffuses into a cell and, if the appropriate molecule is present, yields a product, which is a substrate for luciferase. If a luciferase is present in the cell, luminescence can be detected. Alternatively, in a cell which lacks luciferase, the product passes out of the cell into the medium and that medium is added to a luciferase reaction mixture. Thereafter, the activity resulting from the interaction of the cell with the compound is determined by measuring luminescence of the reaction mixture relative to a control (minus test compound) reaction mixture.

In one aspect, the compound is preferably contacted first with the cell for a predetermined time period. Thereafter, the cell is contacted with the luciferin analogue and luciferase simultaneously or contemporaneously and the mixture allowed to incubate for a second predetermined time period. Enzyme activity is determined by measuring the amount of luminescence generated from the reaction mixture relative to a control reaction mixture (e.g., minus test compound). In another aspect, the test compound is preferably contacted first with the cell for a predetermined time period. Thereafter, the exposed cell is then contacted with the luciferin analogue and incubated for a second predetermined time period. The cell is then contacted with luciferase to form a third mixture which is allowed to incubate for a third predetermined time period. Thereafter, the activity of the cell resulting from the interaction of the cell with the test compound(s) is determined by measuring luminescence of the reaction mixture relative to a control reaction mixture (e.g., minus test compound). Detergent addition can rupture the cells and release cell content.

A cell-based luminescence detection assay for molecules present in the cell medium, e.g., molecules which actively or via inactive mechanisms are present in the cell medium, can include adding a reaction mixture with the luciferin analogue to the cell medium, or adding the cell medium to a reaction mixture with the luciferin analogue, and detecting luminescence.

In yet another embodiment of a cell-based assay, the cells may be lysed in an appropriate lysis buffer. For animal cells, a buffer with 0.1-1.0% non-ionic detergents such as Triton X 100 or Tergitol is typically sufficient. Bacteria, plant, fungal or yeast cells are usually more difficult to lyse. Detergents, freeze/thaw cycles, hypotonic buffers, sonication, cavitation or combinations of these methods may be used. The method of lysis that produces a lysate is compatible with luciferase or other enzyme activity, or the detection of other molecules or conditions.

The presence or activity of nonluciferase enzymes may be measured in cells grown in culture medium or in cells within animals, e.g., living animals. For measurements in cells in animals, a luciferin analogue may be administered to the animal, e.g., injected into the animal or added to an aqueous solution, e.g., water, or food consumed by the animal. Conversion of the analogue to a product that is a luciferase substrate may be detected by luminescence mediated by luciferase expressed in cells in the animal, e.g., transgenic cells, by luciferase administered to the animal, e.g., injected into the animal, or by collecting physiological fluids, e.g., blood, plasma, urine, and the like, or tissue samples, and combining those with a luciferase reagent.

Assays which employ two reactions may be conducted simultaneously (one step) or sequentially (two step) to detect one or more moieties including proteins (peptides or polypeptides), e.g., enzymes, substrates, cofactors, inhibitors or activators for enzymatic reactions, or conditions, e.g., redox conditions. A sequential reaction may be conducted in the same vessel, e.g., a well of a multiwell plate. For a two-step assay, the first reaction mixture may contain all of the reagents or less than all of the reagents for a nonluciferase enzyme-mediated reaction, where one of the reagents that is absent is the one to be detected in a sample, e.g., a cell lysate. For instance, a nonluciferase enzyme-mediated reaction is performed under conditions effective to convert a luciferin analogue that is a substrate for the nonluciferase and a prosubstrate of luciferase, to a product that is a substrate of luciferase. The first reaction may be quenched at the time, or prior to addition, of a luciferase reaction mixture. For instance, a quencher of the first reaction may be present in the luciferase reaction mixture. The luciferase reaction mixture preferably substantially lacks a substrate for the luciferase, e.g., the only source of substrate for the luciferase is provided by a reaction between the nonluciferase enzyme and the analogue. When all the reagents for the first reaction are present in the first reaction mixture, the assay may be employed to identify moieties that alter the reaction, e.g., inhibitors or enhancers of the reaction. After performing the reactions, either simultaneously or sequentially, the presence or amount of one or more molecules, or one or more inhibitors or activators of the reaction(s) is/are detected or determined and/or to what extent and with what potency.

For a one step assay, a reaction mixture may contain reagents for two reactions, such as reagents for a nonluciferase enzyme-mediated reaction and a luciferase-mediated reaction or for a nonenzymatic reaction and a luciferase-mediated reaction, or a reaction mixture for a single reaction, e.g., for a reaction between an analogue of a fluorophore which is a substrate for an enzyme and the enzyme or a luciferase-mediated reaction, e.g., a luciferase is suspected in a sample to be tested.

For assays which employ two reactions, the order of adding the molecules for the assays can vary. If initiated and conducted sequentially (whether in the same vessel or not), adjustments to reaction conditions, e.g., reagent concentration, temperatures or additional reagents, may be performed. In certain embodiments, the two or more reactions are carried out simultaneously in a single reaction mixture. Optionally, the assays are a homogeneous assay, e.g., the components are mixed prior to adding the mixture to the sample. Results may be read without additional transfer of reagents.

The assays of the present disclosure thus allow the detection of one or more molecules or conditions in a sample, e.g., a sample which includes eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof, or a sample which includes a purified form of the molecule, e.g., purified nonluciferase enzyme which is useful to prepare a standard curve. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the disclosure, a moiety which alters the level or activity of the molecule to be detected, and/or a gene product unrelated to the molecule or moiety that alters the level or activity of the molecule.

The present methods can be employed to detect a molecule for an enzyme-mediated reaction, a nonenzymatic-mediated reaction or condition. For instance, molecules or conditions to be detected by the method include but are not limited to enzymes, e.g., demethylases, oxidases (e.g., a MAO), deacetylases, deformylases, proteases (proteosome, calpain, beta-secretase, cathepsin, calpain, thrombin, granzyme B), phosphatases, kinases, peroxidases, transferases, e.g., GST, sulfotases, beta-lactamases, cytochrome P450 enzymes, esterase, e.g., acetylcholinesterase, dehydrogenase, luciferase, substrates, inhibitors, cofactors, activators of enzyme mediated reactions, reactive oxygen species, reducing conditions and transcriptional regulators or regulators of gene transcription. The enzymes employed in the methods, either enzymes to be detected or enzymes which are useful to detect a substrate or cofactor, can be selected from any combination of enzymes including recombinant and endogenous (native) enzymes. In certain embodiments, the enzyme to be detected is an endogenous enzyme. In another embodiment, the enzyme is a recombinant enzyme. Other combinations apparent to one of ordinary skill in the art can be used in the present assays and methods according to the teachings herein. The enzymes include but are not limited to proteases, phosphatases, peroxidases, sulfatases, peptidases, oxidases, dealkylases, deformylases and glycosidases. The enzyme may be a hydrolase, oxidoreductase, lyase, transferase, e.g., glutathione S transferase, isomerase, ligase, or synthase. Of particular interest are classes of enzymes that have physiological significance. These enzymes include protein peptidases, esterases, protein phosphatases, glycosylases, proteases, dehydrogenases, oxidases, oxygenases, reductases, methylases and the like. Enzymes of interest include those involved in making or hydrolyzing esters, both organic and inorganic, glycosylating, and hydrolyzing amides. In any class, there may be further subdivisions.

In particular, enzymes that are useful in the present disclosure include any protein that exhibits enzymatic activity, e.g., lipases, phospholipases, sulphatases, ureases, peptidases, proteases and esterases, including acid phosphatases, glucosidases, glucuronidases, galactosidases, carboxylesterases, and luciferases. In certain embodiments, the enzyme is a hydrolytic enzyme. Examples of hydrolytic enzymes include alkaline and acid phosphatases, esterases, decarboxylases, phospholipase D, P-xylosidase, β-D-fucosidase, thioglucosidase, β-D-galactosidase, α-D-galactosidase, α-D-glucosidase, β-D-glucosidase, β-D-glucuronidase, β-D-mannosidase, β-D-mannosidase, β-D-fructofuranosidase, and β-D-glucosiduronase.

In certain embodiments, the compounds of formula (I') or formula (I) can be used for detecting luminescence in live cells, e.g., in vivo. In some embodiments, a luciferase can be expressed in cells (as a reporter or otherwise), and the cells treated with a luciferin analogue (e.g., a compound of formula (I') or formula (I)), which will permeate cells in culture, react with the luciferase and generate luminescence. In addition to being cell permeant, the compounds of formula (I') or formula (I) may show comparable biocompatibility to native luciferin in terms of cell viability. In some embodiments, the compounds of formula (I') or formula (I) containing chemical modifications known to increase the stability of native luciferin or proluciferins in media can be synthesized and used for more robust, live cell luciferase-based reporter assays. In still other embodiments, a sample (including cells, tissues, animals, etc.) containing a luciferase and a compound of formula (I') or formula (I) may be assayed using various microscopy and imaging techniques, e.g., in vivo imaging. In still other embodiments, a secretable luciferase is expressed in cells as part of a live-cell reporter system.

In certain embodiments, the present compounds can be used in a method for detecting luminescence in a transgenic animal. The method comprises administering a compound of the present compounds to a transgenic animal expressing a luciferin-utilizing luciferase, and detecting luminescence.

In certain embodiments, the compounds of formula (I') or formula (I) disclosed herein may be provided as part of a kit. In some embodiments, the kit may include one or more luciferases (in the form of a polypeptide, a polynucleotide, or both) and a luciferin analogue of formula (I') or formula (I), along with suitable reagents and instructions to enable a user to perform assays such as those disclosed herein. The kit may also include one or more buffers such as those disclosed herein.

In some embodiments, provided herein are assay systems for detecting or quantifying ATP in a sample, comprising: (a) a reagent composition comprising a compound of formula (I') or formula (I) described herein; and (b) a sample comprising or suspected of comprising ATP. In some embodiments, assay systems further comprise a device for the detection and/or measurement of luminescence (e.g., luminometer although other light detection device or instrument may be used). In some embodiments, the sample is a cell lysate.

In some embodiments, provided herein are methods of detecting ATP in a sample comprising: (a) adding to the sample a reagent composition comprising a compound of formula (I') or formula (I) described herein; and (b) detecting luminescence. In some embodiments, the sample comprises cells, and the method further comprises lysing the cells to generate a cell lysate. In some embodiments, provided herein are methods of quantifying the amount or concentration of ATP in a sample comprising: (a) adding to the sample a reagent composition comprising a compound of formula (I') or formula (I) described herein; (b) quantifying luminescence from the sample; and (c) comparing the luminescence to a control value to determine the amount or concentration of ATP in the sample. In some embodiments, the control value is determined from a separate quantification of luminescence produced by a control sample comprising a known concentration of ATP. In some embodiments, methods further comprise the step of adding a known concentration of ATP to the sample. In some embodiments, luminescence is quantified at multiple time-points. In some embodiments, luminescence is quantified in real time.

In some embodiments, provided herein are methods, compositions and kits that are used to effectively and accurately detect and quantify cellular ATP levels. In some embodiments, the luciferases and reagent compositions find use in the detection of ATP on surfaces, in non-cellular samples (e.g., water), for hygiene monitoring, etc. In some embodiments, methods comprise the addition of a single reagent composition that comprises a luciferase and luciferin or luciferin analogue (and possibly dehydroluciferin) to a sample (e.g., a sample comprising or suspected of possibly comprising ATP) and detecting luminescence. In some embodiments, additional components and/or reagents (see above) are included with the reagent composition or added separately (e.g., a kinase inhibitor, a compound that prevents accumulation of ATP, a cell-lysing agent (e.g., a polyoxyethylene such as THESIT), an ATP extracting agent, magnesium, a buffer, salts, etc.). In some embodiments, the inclusion of the luciferase and luciferin or luciferin analogue in a single reagent speeds ATP detection, simplifies assays and handling, and increases reproducibility.

As addressed throughout, the methods, compositions and kits herein are particularly useful for the qualitative or quantitative detection of ATP (or ATP an analogue which can function as a luciferase substrate) in a sample. In some embodiments, a simple qualitative experiment in which luminescence is generated in a sample using a reagent composition (e.g., comprising luciferase and luciferin) indicates the presence of ATP. In some embodiments an assay is provided in which the amount of ATP in a sample is quantitated. ATP may be detected (e.g., qualitatively) and/or quantitated as a single time-point, at multiple time-points, or in real time using the luciferases, reagent compositions, and/or kits herein.

In some embodiments, a sample is anything that contains or is suspected of containing ATP or a suitable ATP analogue, such as cell lysates, intact cells, biopsies, foods, beverages, water, swabs wiped on surfaces such as those of animals, plants, or inanimate objects, and the like. Other examples of samples include compositions of a known ATP concentration. Cells or cell lysates may be from any organism, prokaryotic or eukaryotic. Eukaryotic cells may be from plants, animals, fungi, insects, etc. or cultured cells from such organisms. These examples are furnished only as examples and are not meant to be limiting.

A cell lysate comprises cellular components that are no longer organized into a recognizable intact cellular architecture. Cell lysates may have soluble and insoluble components, either of which may be removed before using the lysate. Lysates may be prepared by any means, including physical disruption using sonication, a dounce, mortar and pestle, freeze-thaw cycling, or any other device or process that destroys the physical integrity of cells; or lysis by detergents, such as those in which luciferase activity is maintained, such as zwitterionic and nonionic detergents, or cationic detergents DTAB or CTAB. Preferably, the cell lysate is produced in such a way that the integrity of the ATP concentration is preserved at the time the cells are harvested.

In some embodiments, to accurately detect ATP in a sample, enzymes that would degrade cellular ATP or those that would generate ATP are preferably inhibited or removed. Inhibitors of ATP-generating enzymes, those enzymes that have as a product or by-product ATP, such as the activity of kinases, may be incorporated into the reagent composition (e.g., comprising luciferase and luciferin or luciferin analogue) or into a kit comprising a reagent composition.

The luciferases, reagent compositions, methods, and kits herein permit a user to quantify the amount of ATP in a sample by quantifying the amount of luminescence. In some embodiments, the luciferase and luciferin or luciferin analogue (in a single composition) are applied to a test sample of interest. In some embodiments, the luciferase and luciferin or luciferin analogue (in a single composition) are also applied to a sample containing known amounts of ATP (control). The magnitude of the signal generated from the test sample correlates to the concentration of ATP in the sample. In some embodiments, the magnitude of the luminescent signal from the sample of unknown ATP concentration is correlated to signal generated either by internal controls (the addition of a known amount of ATP to a sample and measuring the subsequent luminescence) or external standard curves generated by measuring the luminescence of several samples of known ATP concentrations and plotting them graphically.

4. EXAMPLES

Example 1. Synthesis Method I

In general, 5,5-Disubstituted luciferin analogs were synthesized as described in Scheme 1. 2-cyanobenzothiazole (CBT) derivatives (A) were either commercially available or synthesized via protocols described previously (Woodroofe, et al., *Biochemistry*, 2008, 47, 10383-10393; Woodroofe, et al., WO 2014/159044 A1; Mofford, et al., *J. Am. Chem. Soc.* 2014, 136, 13277-13282). β,β-Disubstituted cysteine analogs (B) were synthesized via protocols described previously (Stanfield, C. F. et al. *J. Org. Chem.* 1986, 51, 5153-5156).

Hydrochloric salts of β,β-disubstituted cysteine analogs (B, 0.15 mmol, 1.5 equiv) dissolved in $H_2O$ (1 mL) under $N_2$ were neutralized with 1 N NaOH (aq, 0.30 mmol, 300 μL, 3.0 equiv). To a solution of CBT derivatives (A) (0.1 mmol, 1.0 equiv) in DMF (2 mL) at RT under $N_2$, was added the neutralized solution of β,β-disubstituted cysteine analogs. The solution was then stirred under $N_2$ for 30 min. LC-MS indicated complete consumption of the CBT substrates (A). Pure products (I) were obtained via preparative HPLC (mobile phase A: 10 mM $NH_4OAc$ aqueous solution; mobile phase B: $CH_3CN$; gradient condition: 5% B to 95% B over 30 minutes).

The following Table 1 lists representative compounds that were prepared using the general procedure of Scheme I.

TABLE 1

| Compound | Structure | Yield (%) | MS [M + H] | RLU% * |
|---|---|---|---|---|
| CS0333 | 5-(6-hydroxybenzo[d]thiazol-2-yl)-4-thia-6-azaspiro[2.4]hept-5-ene-7-carboxylic acid | 73 | 307.03 | 0.27 |
| CS0329 | 6-(6-hydroxybenzo[d]thiazol-2-yl)-5-thia-7-azaspiro[3.4]oct-6-ene-8-carboxylic acid | 38 | 321.04 | 0.29 |
| CS0326 | 2-(6-hydroxybenzo[d]thiazol-2-yl)-1-thia-3-azaspiro[4.4]non-2-ene-4-carboxylic acid | 70 | 335.06 | 0.43 |
| CS0325 | 2-(6-hydroxybenzo[d]thiazol-2-yl)-1-thia-3-azaspiro[4.5]dec-2-ene-4-carboxylic acid | 82 | 349.07 | 0.22 |
| CS0330 | 5,5-diethyl-2-(6-hydroxybenzo[d]thiazol-2-yl)-4,5-dihydrothiazole-4-carboxylic acid | 74 | 337.07 | 0.60 |

TABLE 1-continued

| Compound | Structure | Yield (%) | MS [M + H] | RLU% * |
|---|---|---|---|---|
| CS0266 | (S)-2-(5-fluoro-6-hydroxybenzo[d]thiazol-2-yl)-5,5-dimethyl-4,5-dihydrothiazole-4-carboxylic acid | 83 | 327.36 | N/A |
| CS0268 | (R)-2-(5-fluoro-6-hydroxybenzo[d]thiazol-2-yl)-5,5-dimethyl-4,5-dihydrothiazole-4-carboxylic acid | 68 | 327.36 | N/A |
| CS0332 | (S)-2-(7-aminonaphtho[2,1-d]thiazol-2-yl)-5,5-dimethyl-4,5-dihydrothiazole-4-carboxylic acid | 88 | 358.44 | N/A |
| CS0357 | (S)-5,5-dimethyl-2-(6-(pyrrolidin-1-yl)benzo[d]thiazol-2-yl)-4,5-dihydrothiazole-4-carboxylic acid | 46 | 362.47 | N/A |
| CS0359 | (S)-2-(6,7-dihydro-5H-thiazolo[4,5-f]indol-2-yl)-5,5-dimethyl-4,5-dihydrothiazole-4-carboxylic acid | 75 | 334.43 | N/A |

TABLE 1-continued

| Compound | Structure | Yield (%) | MS [M + H] | RLU% * |
|---|---|---|---|---|
| CS0361 | (S)-2-(6-((3-hydroxypropyl)amino)benzo[d]thiazol-2-yl)-5,5-dimethyl-4,5-dihydrothiazole-4-carboxylic acid | 64 | 366.47 | N/A |
| CS0392 | 2-(5-fluoro-6-hydroxybenzo[d]thiazol-2-yl)-1-thia-3-azaspiro[4.5]dec-2-ene-4-carboxylic acid | 53 | 367.43 | 0.13 |
| CS0396 | 5,5-dibenzyl-2-(6-hydroxybenzo[d]thiazol-2-yl)-4,5-dihydrothiazole-4-carboxylic acid | 75 | 461.57 | 1.0 |
| CS0388 | 5,5-diethyl-2-(5-fluoro-6-hydroxybenzo[d]thiazol-2-yl)-4,5-dihydrothiazole-4-carboxylic acid | 63 | 355.42 | 0.64 |
| CS0397 | 2-(6-hydroxybenzo[d]thiazol-2-yl)-1-thia-3-azaspiro[4.6]undec-2-ene-4-carboxylic acid | 73 | 363.47 | 0.13 |
| CS0404 | 2-(6-hydroxybenzo[d]thiazol-2-yl)-8-methyl-1-thia-3-azaspiro[4.5]dec-2-ene-4-carboxylic acid | 80 | 363.47 | 0.31 |

TABLE 1-continued

| Compound | Structure | Yield (%) | MS [M + H] | RLU% * |
|---|---|---|---|---|
| CS0420 | 2-(6-hydroxybenzo[d]thiazol-2-yl)-8-methyl-1-thia-3,8-diazaspiro[4.5]dec-2-ene-4-carboxylic acid | 34 | 364.46 | 0.20 |
| CS0427 | 2-(6-hydroxybenzo[d]thiazol-2-yl)-5,5-dipropyl-4,5-dihydrothiazole-4-carboxylic acid | 77 | 365.49 | 0.16 |
| CS0439 | 2-(6-hydroxybenzo[d]thiazol-2-yl)-8-oxa-1-thia-3-azaspiro[4.5]dec-2-ene-4-carboxylic acid | 67 | 351.45 | 0.09 |

* RLU was normalized to the one generated by 1 mM racemic luciferins under identical conditions.

Example 2. Thermal Stability

Figure 2A:
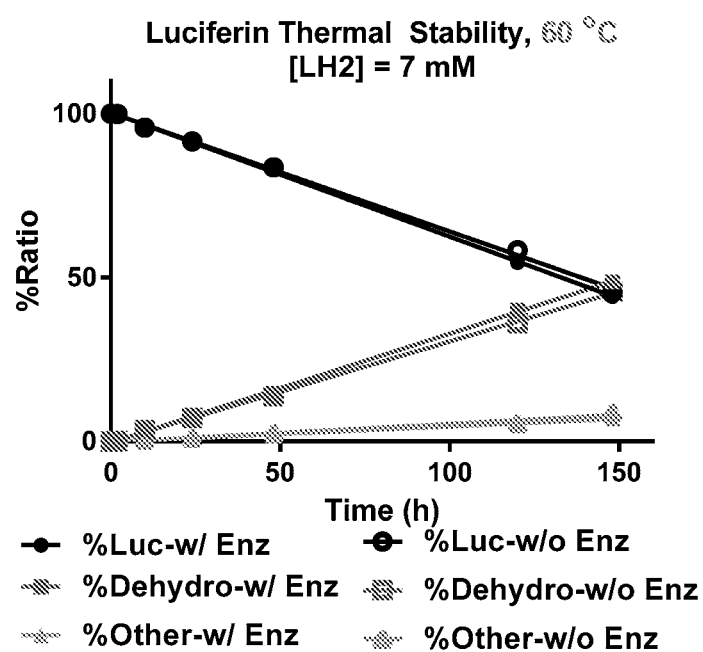
FIG. 2A shows representative thermal stability profile of luciferins.

Representative thermal stability profiling of luciferins: Luciferin stock solutions (pH=6.0, [LH$_2$]$_{final}$=7.0 mM) containing various amounts of detergents, with or without ULTRA-GLO™ luciferase ([enzyme]$_{final}$=0.1 mg/mL; Promega) were incubated at 60° C. Aliquots (20 µL) were taken out at various time points, diluted with H$_2$O (180 µL), and analyzed by RP-HPLC. The percentages of the components were calculated based on UV absorbance at 330 nm for 6'-OH-luciferins or 295 nm for 6'-NH$_2$-luciferins. As shown in FIG. 2A, dehydroluciferin was the major degradation product of luciferin, and the luciferase had little effect on the degradation of luciferins.

Figure 2B:
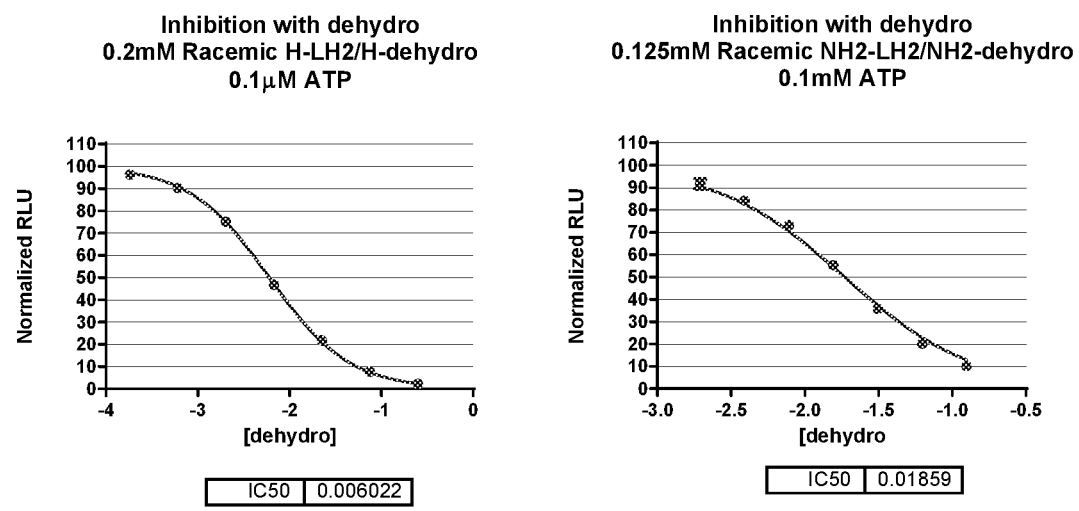
FIG. 2B shows the inhibition of luciferase activity by dehydroluciferin.

Inhibition of luciferase activity by dehydroluciferins: ULTRA-GLO™ luciferase (Promega, 0.1 mg/mL)+0.1% PRIONEX® in detection reagent buffer was prepared. The solution was divided into 2 portions with 0.25 mM Racemic H-Luciferin added to one portion and 0.25 mM racemic NH2 luciferin to the other portion. H-dehydroluciferin (0.25 mM) was added to an aliquot of the racemic H-Luciferin solution, and NH2-dehydroluciferin (0.25 mM) was added to an aliquot of the racemic NH2 luciferin solution. 2× serial dilutions of each of the dehydroluciferin samples were prepared using the racemic solutions as a diluent (500 µL of dehydroluciferin solution added to 500 µL of ULTRA-GLO™+racemic luciferin). 50 µL of each titration series was then added to 50 pt 0.1 mM ATP. The samples were incubated for 1 minute, and the luminescence was measured on GLOMAX®-Multi+ plate luminometer (n=6). As shown in FIG. 2B, dehydroluciferins were potent inhibitors of luciferases, which may account for the decreased light output after storage of luciferins stock solutions for a long period at ambient temperature.

Thermal stability comparison: Luciferins (LH2) or 5,5-disubstituted luciferins (Luc-III, FIG. 3A) stock solutions (pH=6.0, [luciferin]$_{final}$=7.0 mM) containing various amounts of detergents and ULTRA-GLO™ luciferase ([enzyme]$_{final}$=0.1 mg/mL) were incubated at 60° C. Aliquots (20 µL) were taken out at various time points, diluted with H$_2$O (180 µL), and analyzed by RP-HPLC. The percentage of the components were calculated based on UV absorbance at 330 nm for 6'-OH-luciferins or 295 nm for 6'-NH$_2$-luciferins. The results indicated that the 5,5-dimethyl luciferins III-a (6-OH compound) and III-b (6-NH$_2$ compound) were more thermally stable than the unsubstituted luciferin (FIG. 3B).

Example 3. Luminescent Properties

The disclosed compounds were tested to determine their activities as substrates for various luciferase enzymes including Click Beetle Green luciferase, Click Beetle Red luciferase, ULTRA-GLO™ luciferase, and Firefly luciferase. A 0.05 mg/mL solution of each enzyme was prepared in BRIGHT-GLO™ assay buffer (Promega E263A) with 3 mM ATP. 3× serial dilutions of each enzyme were then prepared in BRIGHT-GLO™ assay buffer with 3 mM ATP, and 300 µL of each stock was serially diluted into 700 ul of buffer. A solution of each substrate (0.5 mM) was prepared in Luciferin free water, and 50 µL of the each substrate solution was combined with 504 of the enzyme dilution. Samples were incubated for one minute at room temperature, and luminescence measured on GLOMAX®-Multi+ plate luminometer. As shown in FIGS. 4A-4D, the enzymes tested (Click Beetle Green, Click Beetle Red, ULTRA-GLO', and Firefly luciferase) were able to utilize the disclosed dimethyl substrates to produce light. In these tests, the Click Beetle enzymes produced stronger signals utilizing the dimethyl substrates than the ULTRA-GLO™ and the Firefly luciferases.

Further tests were conducted at various substrate concentrations in the presence of sub-saturating D-Luciferin as a means to compare the binding affinity of the substrates. Solutions of 0.005 mg/ml Click Beetle-Green luciferase (CBG) or UltraGlo luciferase were prepared in Bright-Glo™ assay buffer (Promega E263A) with 3 mM ATP. A 2 mM solution of each substrate was then prepared in water containing D-Luciferin (sub-saturating). Each substrate+D-Luciferin was two-fold serially diluted in luciferin free water. A sample of 50 µL of each substrate dilution was combined with 50 µL of the enzyme solution. Samples were incubated at room temperature for one minute, and luminescence was measured on a GLOMAX® Multi+ plate luminometer. Substrates that have larger side chains at the 5,5 position have higher apparent RLUmax values which indicates that they are less inhibitory to D-Luciferin compared to smaller 5,5 disubstituted side chains. The apparent Km values suggest that analogs bearing smaller 5,5 position side chains bind the luciferase enzyme more tightly in the presence of D-luciferin compared to the larger 5,5 position substitutions. (FIG. 5A-F). RLU values for certain representative compounds (normalized to racemic luciferins under identical conditions) are provided in Table 1 above. For certain representatative compounds, substrate titration tests were performed using procedures as described herein without comparison to luciferins, therefore providing RLU values not normalized to those of luciferins.

Figure 6A:
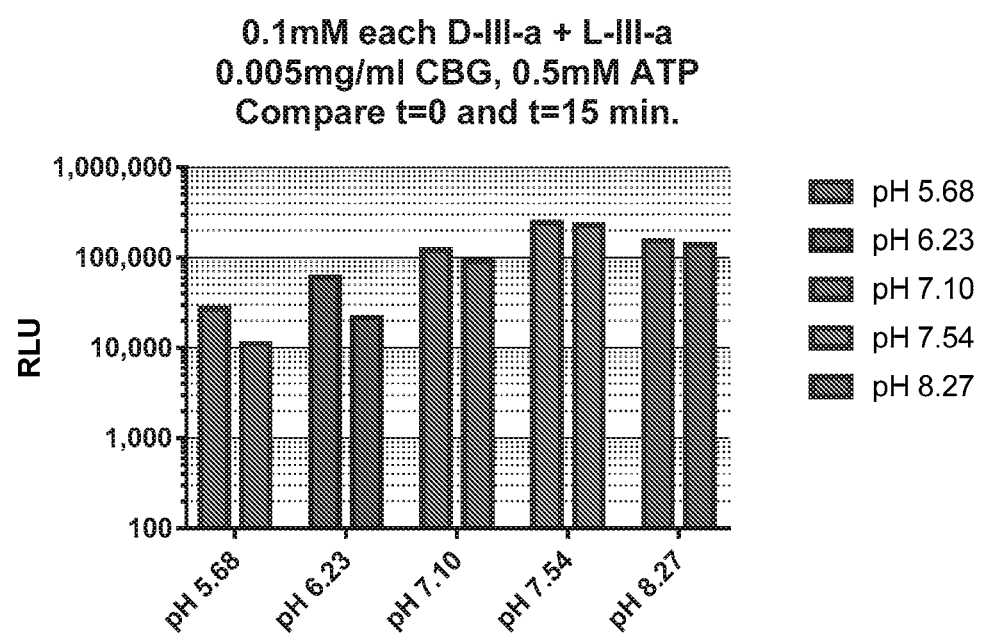
FIGS. 6A-6B show the results of luciferase assays at various pH.
Figure 6B:
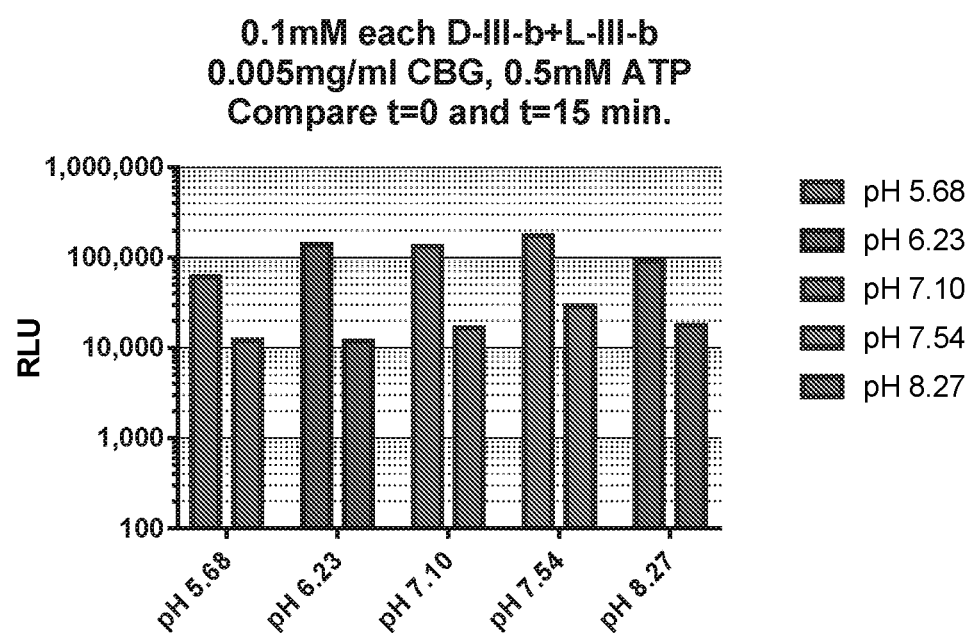

The activities of the disclosed compounds at various pH were also tested. A stock buffer containing 25 mM of one of the following buffers: Citrate, MES, PIPES, HEPES, and TAPS was prepared, which also contained 0.5% (v/v) Tergitol, 0.05% Mazu DF204, and 10 mM MgSO$_4$. The buffers were aliquoted, and NaOH was added at various amounts to achieve a pH series. The accurate pH for each solution was determined by a pH meter. ATP (1 mM) and Click Beetle Green luciferase (CBG, 0.01 mg/mL) were added to each buffer in the pH series. Racemic mixtures of each dimethyl substrate (0.2 mM) were prepared in Luciferin free water. In triplicate, each diluted substrate (50 uL) and each buffer in the pH series (50 uL) were combined, and the luminescence was measured using GLOMAX®-Multi+ plate luminometer immediately (t=0) and after a 15 minute incubation at room temperature (t=15). The results showed that the racemic mixtures of dimethyl substrates are active luciferase substrates over a pH range from about pH 5.6 to about pH 8.3 (FIGS. 6A-6B). Thus, the disclosed compounds, in both L and D forms, may be utilized by firefly luciferases or click beetle luciferase to produce bioluminescence over a broad range of pH (FIGS. 6A-6B).

Figure 7:
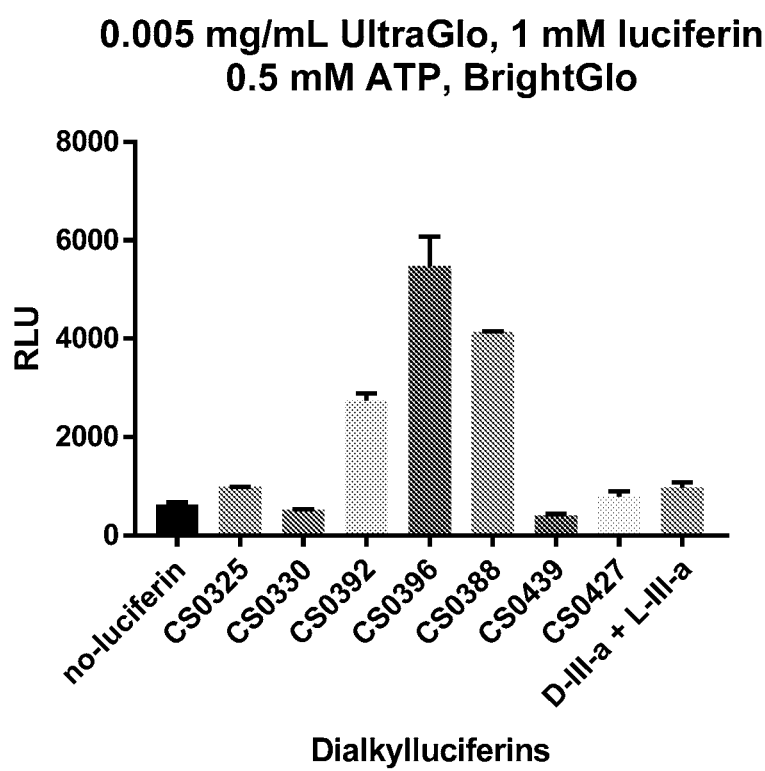
FIG. 7 shows luminescence assays results of representative luciferin analogs with substitutions at the 5,5 position as substrates for UltraGlo™ luciferase.

To determine if luciferin analogs with substitutions at the 5,5 position could be substrates for UltraGlo™ luciferase, tests were performed with analogs containing various di-substitutions of alkyl groups and closed ring structures in luminescence assays. A solution of 0.005 mg/ml UltraGlo™ luciferase (Promega Corp) prepared in 1×TBS+1% Prionex was combined with 0.5 mM ATP in Bright-Glo™ assay buffer (Promega E263A). All substrates were diluted separately in DMSO to 20 mM. After a 30-minute incubation at room temperature, diluted substrate was added to 1 mM final concentration in the reaction and mixed by pipetting. Reactions were further incubated at room temperature for 1 minute, and luminescence measured on a GLOMAX® Multi+ plate luminometer. Several of the luciferin analogs with larger substitutions at the 5,5 position such as cyclohexyl (CS0392), dibenzyl (CS0396), and diethyl (CS0388) all showed measurable luminescence values, demonstrating UltraGlo can utilize them as substrates (FIG. 7).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for detecting luminescence in a sample, the method comprising contacting the sample with a compound of formula (I'):

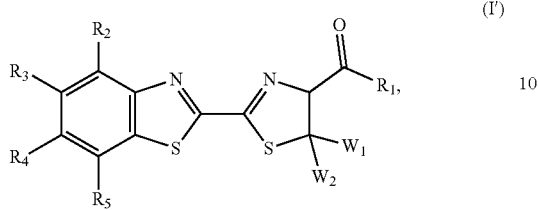

or a tautomer or a salt thereof, wherein $R_1$ is hydrogen, halogen, alkyl, alkenyl, alkynyl, heteroalkyl, aryl, heteroaryl, heterocycle, cycloalkyl, cycloalkenyl, —$OR_{1a}$, —$NR_{1b}R_{1c}$, or —$NR_{1x}G^{10}$;

$R_2$ is hydrogen, halogen, cyano, nitro, alkyl, alkenyl, alkynyl, heteroalkyl, aryl, heteroaryl, heterocycle, cycloalkyl, cycloalkenyl, —$OR_{2a}$, —$NR_{2b}R_{2c}$, —$SR_{2d}$, —$SO_2R_{2e}$, —$S(O)R_{2f}$, or —$P(O)OR_{2g}R_{2h}$;

$R_3$ is hydrogen, halogen, cyano, nitro, alkyl, alkenyl, alkynyl, heteroalkyl, aryl, heteroaryl, heterocycle, cycloalkyl, cycloalkenyl, —$OR_{3a}$, —$NR_{3b}R_{3c}$, —$SR_{3d}$, —$SO_2R_{3e}$, —$S(O)R_{3f}$, or —$P(O)OR_{3g}R_{3h}$;

$R_4$ is hydrogen, halogen, cyano, nitro, alkyl, alkenyl, alkynyl, heteroalkyl, aryl, heteroaryl, heterocycle, cycloalkyl, cycloalkenyl, —$OR_{4a}$, —$NR_{4b}R_{4c}$, —$SR_{4d}$, —$SO_2R_{4e}$, —$S(O)R_{4f}$, or —$P(O)OR_{4g}R_{4h}$;

$R_5$ is hydrogen, halogen, cyano, nitro, alkyl, alkenyl, alkynyl, heteroalkyl, aryl, heteroaryl, heterocycle, cycloalkyl, cycloalkenyl, —$OR_{5a}$, —$NR_{5b}R_{5c}$, —$SR_{5d}$, —$SO_2R_{5e}$, —$S(O)R_{5f}$, or —$P(O)OR_{5g}R_{5h}$;

or $R_2$ and $R_3$ together with the atoms to which they are attached, $R_3$ and $R_4$ together with the atoms to which they are attached, or $R_4$ and $R_5$ together with the atoms to which they are attached, form a 5- or 6-membered saturated, partially unsaturated or fully unsaturated ring, the 5- or 6-membered ring optionally containing 1, 2 or 3 heteroatoms or heteroatom groups each independently selected from the group consisting of O, N, S, NO, SO and $SO_2$ as ring members, the 5- or 6-membered ring optionally fused to an aryl, heteroaryl, heterocycle, or cycloalkyl, the 5- or 6-membered ring substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylanino, aminoakyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl;

$R_{1a}$, $R_{1b}$, $R_{1c}$, $R_{2a}$, $R_{2b}$, $R_{2c}$, $R_{2d}$, $R_{2e}$, $R_{2f}$, $R_{2g}$, $R_{2h}$, $R_{3a}$, $R_{3b}$, $R_{3c}$, $R_{3d}$, $R_{3e}$, $R_{3f}$, $R_{3g}$, $R_{3h}$, $R_{4a}$, $R_{4b}$, $R_{4c}$, $R_{4d}$, $R_{4e}$, $R_{4f}$, $R_{4h}$, $R_{5a}$, $R_{5b}$, $R_{5c}$, $R_{5d}$, $R_{5e}$, $R_{5f}$, $R_{5g}$, and $R_{5h}$, are each independently selected from the group consisting of hydrogen, alkyl, alkenyl, alkynyl, heteroalkyl, aryl, heteroaryl, heterocycle, cycloalkyl, and cycloalkenyl;

$R_{1x}$, $R_{2x}$, $R_{3x}$, $R_{4x}$, and $R_{5x}$ are each independently hydrogen or $C_1$-$C_{12}$alkyl;

—$NR_{1x}G^{10}$

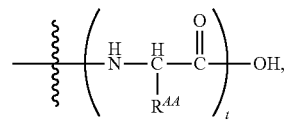

wherein $R^{AA}$ at each occurrence is independently hydrogen, alkyl, or alkyl substituted with a substituent selected from the group consisting of —OH, —$NH_2$, —SH, —$SCH_3$, phenyl, —COOH, —CO—$NH_2$,

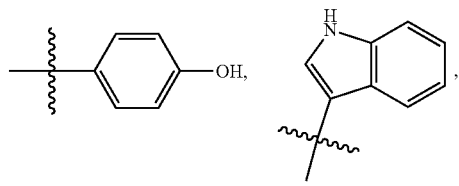

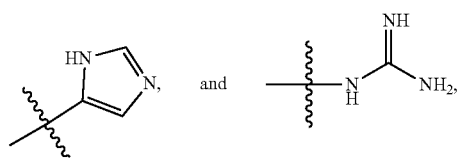

and t is 1-10; and $W_1$ and $W_2$ are each independently selected from the group consisting of alkyl, alkenyl, alkynyl, alkoxy, heteroalkyl, aryl, heteroaryl, heterocycle, cycloalkyl, and cycloalkenyl;

wherein said alkyl, alkenyl, alkynyl, alkoxy, heteroalkyl, aryl, heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl;

contacting the sample with a luciferin-utilizing luciferase, if it is not present in the sample; and detecting luminescence.

2. The method of claim 1, wherein the compound is a compound of formula (I),

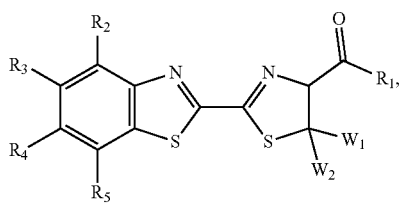

or a tautomer or a salt thereof, wherein $R_1$ is hydrogen, halogen, alkyl, alkenyl, alkynyl, heteroalkyl, aryl, heteroaryl, heterocycle, cycloalkyl, cycloalkenyl, $-OR_{1a}$, or $-NR_{1b}R_{1c}$;

$R_2$ is hydrogen, halogen, cyano, nitro, alkyl, alkenyl, alkynyl, heteroalkyl, aryl, heteroaryl, heterocycle, cycloalkyl, cycloalkenyl, $-OR_{2a}$, $-NR_{2b}R_{2c}$, $-SR_{2d}$, $-SO_2R_{2e}$, $-S(O)R_{2f}$, or $-P(O)OR_{2g}R_{2h}$;

$R_3$ is hydrogen, halogen, cyano, nitro, alkyl, alkenyl, alkynyl, heteroalkyl, aryl, heteroaryl, heterocycle, cycloalkyl, cycloalkenyl, $-OR_{3a}$, $-NR_{3b}R_{3c}$, $-SR_{3d}$, $-SO_2R_{3e}$, $-S(O)R_{3f}$, or $-P(O)OR_{3g}R_{3h}$;

$R_4$ is hydrogen, halogen, cyano, nitro, alkyl, alkenyl, alkynyl, heteroalkyl, aryl, heteroaryl, heterocycle, cycloalkyl, cycloalkenyl, $-OR_{4a}$, $-NR_{4b}R_{4c}$, $-SR_{4d}$, $-SO_2R_{4e}$, $-S(O)R_{4f}$, or $-P(O)OR_{4g}R_{4h}$;

$R_5$ is hydrogen, halogen, cyano, nitro, alkyl, alkenyl, alkynyl, heteroalkyl, aryl, heteroaryl, heterocycle, cycloalkyl, cycloalkenyl, $-OR_{5a}$, $-NR_{5b}R_{5c}$, $-SR_{5d}$, $-SO_2R_{5e}$, $-S(O)R_{5f}$, or $-P(O)OR_{5g}R_{5h}$;

or $R_2$ and $R_3$ together with the atoms to which they are attached, $R_3$ and $R_4$ together with the atoms to which they are attached, or $R_4$ and $R_5$ together with the atoms to which they are attached, form a 5- or 6-membered saturated, partially unsaturated or fully unsaturated ring, the 5- or 6-membered ring optionally containing 1, 2 or 3 heteroatoms or heteroatom groups each independently selected from the group consisting of O, N, S, NO, SO and $SO_2$ as ring members, the 5- or 6-membered ring optionally fused to an aryl, heteroaryl, heterocycle, or cycloalkyl, the 5- or 6-membered ring substituted with 0, 1, 2, 3, or 4 substituents, each independently selected from the group consisting of halogen, $=O$, $=S$, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, $-COOH$, ketone, amide, carbamate, silyl, substituted silyl, t-butyldimethylsilyl, alkylsulfanyl, sulfanyl, and acyl;

$R_{1a}$, $R_{1b}$, $R_{1c}$, $R_{2a}$, $R_{2b}$, $R_{2c}$, $R_{2d}$, $R_{2e}$, $R_{2f}$, $R_{2g}$, $R_{2h}$, $R_{3a}$, $R_{3b}$, $R_{3c}$, $R_{3d}$, $R_{3e}$, $R_{3f}$, $R_{3g}$, $R_{3h}$, $R_{4a}$, $R_{4b}$, $R_{4c}$, $R_{4d}$, $R_{4e}$, $R_{4f}$, $R_{4g}$, $R_{4h}$, $R_{5a}$, $R_{5b}$, $R_{5c}$, $R_{5d}$, $R_{5e}$, $R_{5f}$, $R_{5g}$ and $R_{5h}$, are each independently selected from the group consisting of hydrogen, alkyl, alkenyl, alkynyl, heteroalkyl, aryl, heteroaryl, heterocycle, cycloalkyl, and cycloalkenyl; and $W_1$ and $W_2$ are each independently selected from the group consisting of alkyl, alkenyl, alkynyl, alkoxy, heteroalkyl, aryl, heteroaryl, heterocycle, cycloalkyl, and cycloalkenyl;

wherein said alkyl, alkenyl, alkynyl, alkoxy, heteroalkyl, aryl, heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, $=O$, $=S$, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, $-COOH$, ketone, amide, carbamate, silyl, substituted silyl, t-butyldimethylsilyl, alkylsulfanyl, sulfanyl, and acyl.

3. The method of claim 1, wherein $R_1$ is $-OH$.

4. The method of claim 2, wherein $R_2$, $R_3$, $R_4$, and $R_5$, are each independently selected from the group consisting of hydrogen, halogen, cyano, nitro, $C_1$-$C_4$-alkyl, $C_2$-$C_4$-alkenyl, $C_2$-$C_4$-alkynyl, $-OH$, and $-NH_2$.

5. The method of claim 2, wherein $R_4$ is $-OR_{4a}$, or $-NR_{4b}R_{4c}$.

6. The method of claim 2, wherein $R_3$ and $R_4$ together with the atoms to which they are attached form a 5- or 6-membered optionally substituted saturated, partially unsaturated or fully unsaturated ring.

7. The method of claim 2, wherein $R_4$ and $R_5$ together with the atoms to which they are attached form a 5- or 6-membered optionally substituted saturated, partially unsaturated or fully unsaturated ring.

8. The method of claim 2, wherein $R_3$ and $R_4$ together with the atoms to which they are attached form a 6-membered optionally substituted heterocycle, and $R_4$ and $R_5$ together with the atoms to which they are attached form a 6-membered optionally substituted heterocycle, wherein the two 6-membered rings are fused.

9. The method of claim 2, wherein $W_1$ and $W_2$ are each alkyl.

10. The method of claim 2, wherein the compound of formula (I) is a compound of formula (I-a),

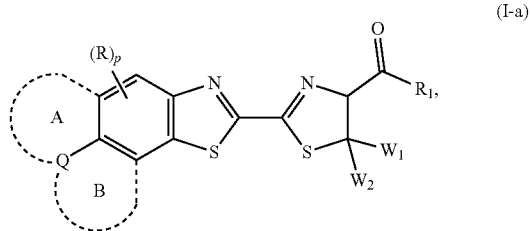

or a tautomer or a salt thereof, wherein

A and B are each independently an optional 5- or 6-membered ring selected from the group consisting of aryl, heteroaryl, and heterocycle; wherein A, when present, is optionally substituted with one or more $R_A$; B, when present, is optionally substituted with one or more $R_B$; and each of R and $R_B$, where present, is independently alkyl, halo, haloalkyl, hydroxyalkyl, $-OH$, $-NH_2$, or alkyl $-NH-$;

Q is —OR$_{Q1}$ or —NR$_{Q1}$R$_{Q1}$ when both A and B are absent, wherein R$_{Q1}$ at each occurrence is independently hydrogen, alkyl, or hydroxyalkyl; or Q is C, CR$_{Q2}$, CR$_{Q2}$R$_{Q2}$, N, NR$_{Q2}$, or O when at least one of A and B is present, wherein R$_2$ at each occurrence is independently hydrogen, alkyl, or hydroxyalkyl;

R is alkyl, alkoxy, halo, haloalkyl, hydroxyalkyl, hydroxy, cyano, nitro, amino, alkylamino, dialkylamino, alkenyl, alkynyl, heteroalkyl, aryl, heteroaryl, heterocycle, cycloalkyl, or cycloalkenyl; and p is 0, 1, 2, or 3.

11. The method of claim 10, wherein the compound is a compound of formula (I-b) or (I-c):

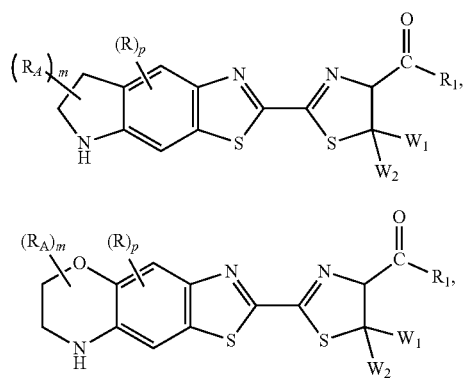

wherein
in is 0, 1, 2, or 3; and
p is 0, 1, or 2.

12. The method of claim 10, wherein the compound is a compound of formula (I-d):

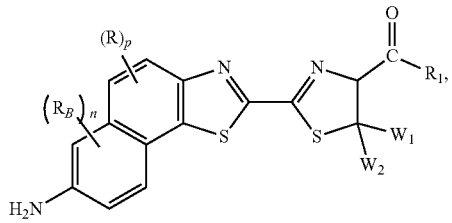

wherein
n is 0, 1, 2, or 3; and
p is 0, 1, or 2.

13. The method of claim 10, wherein the compound is a compound of formula (I-e):

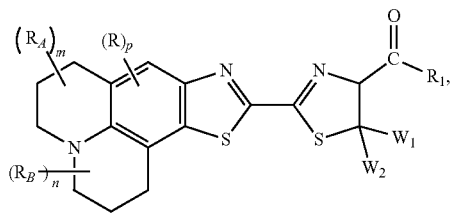

wherein
m is 0, 1, 2, or 3;
n is 0, 1, 2, or 3; and
p is 0, or 1.

14. The method of claim 10, wherein the compound is a compound of formula (I-f):

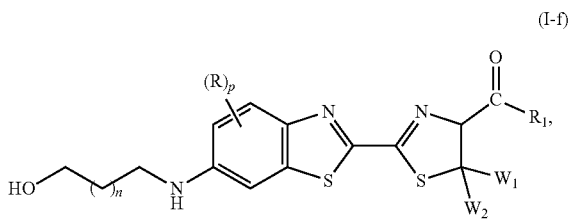

wherein n is 0, 1, 2, 3, 4, 5, 6, 7, or 8.

15. The method of claim 10, wherein the compound is a compound of formula (I-g):

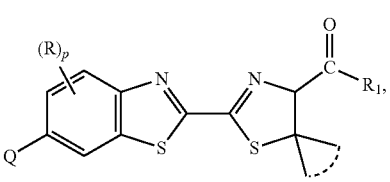

wherein

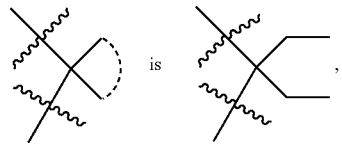

which is optionally substituted.

16. The method of claim 2, wherein the compound is selected from the group consisting of:
  5,5-diethyl-2-(6-hydroxybenzo[d]thiazol-2-yl)-4,5-dihydrothiazole-4-carboxylic acid;
  (S)-2-(5-fluoro-6-hydroxybenzo[d]thiazol-2-yl)-5,5-dimethyl-4,5-dihydrothiazole-4-carboxylic acid;
  (R)-2-(5-fluoro-6-hydroxybenzo[d]thiazol-2-yl)-5,5-dimethyl-4,5-dihydrothiazole-4-carboxylic acid;
  (S)-2-(7-aminonaphtho[2,1-d]thiazol-2-yl)-5,5-dimethyl-4,5-dihydrothiazole-4-carboxylic acid;
  (S)-5,5-dimethyl-2-(6-(pyrrolidin-1-yl)benzo[d]thiazol-2-yl)-4,5-dihydrothiazole-4-carboxylic acid;
  (S)-2-(6,7-dihydro-5H-thiazolo[4,5-f]indol-2-yl)-5,5-dimethyl-4,5-dihydrothiazole-4-carboxylic acid;
  (S)-2-(6-((3-hydroxypropyl)amino)benzo[d]thiazol-2-yl)-5,5-dimethyl-4,5-dihydrothiazole-4-carboxylic acid;
  5,5-dibenzyl-2-(6-hydroxybenzo[d]thiazol-2-yl)-4,5-dihydrothiazole-4-carboxylic acid;
  5,5-diethyl-2-(5-fluoro-6-hydroxybenzo[d]thiazol-2-yl)-4,5-dihydrothiazole-4-carboxylic acid; and
  2-(6-hydroxybenzo[d]thiazol-2-yl)-5,5-dipropyl-4,5-dihydrothiazole-4-carboxylic acid;
  or a tautomer or a salt thereof.

17. The method of claim 2, wherein the sample contains live cells.

18. The method of claim 2, wherein the sample contains a luciferin-utilizing luciferase.

19. A method for detecting luminescence in a transgenic animal comprising
administering to a transgenic animal a compound of formula (I'):

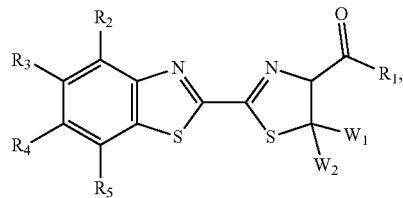

or a tautomer or a salt thereof, wherein
$R_1$ is hydrogen, halogen, alkyl, alkenyl, alkynyl, heteroalkyl, aryl, heteroaryl, heterocycle, cycloalkyl, cycloalkenyl, —$OR_{1a}$, —$NR_{1b}R_{1c}$, or —$NR_{1x}G^{10}$;
$R_2$ is hydrogen, halogen, cyano, nitro, alkyl, alkenyl, alkynyl, heteroalkyl, aryl, heteroaryl, heterocycle, cycloalkyl, cycloalkenyl, —$OR_{2a}$, —$NR_{2b}R_{2c}$, —$SR_{2d}$, —$SO_2R_{2e}$, —$S(O)R_{2f}$, —$P(O)OR_{2g}R_{2h}$;
$R_3$ is hydrogen, halogen, cyano, nitro, alkyl, alkenyl, alkynyl, heteroalkyl, aryl, heteroaryl, heterocycle, cycloalkyl, cycloalkenyl, —$OR_{3a}$, —$NR_{3b}R_{3c}$, —$SR_{3d}$, —$SO_2R_{3e}$, —$S(O)R_{3f}$, —$P(O)OR_{3g}R_{3h}$;
$R_4$ is hydrogen, halogen, cyano, nitro, alkyl, alkenyl, alkynyl, heteroalkyl, aryl, heteroaryl, heterocycle, cycloalkyl, cycloalkenyl, —$OR_{4a}$, —$NR_{4b}R_{4c}$, —$SR_{4d}$, —$SO_2R^{4e}$, —$S(O)R_{4f}$, or —$P(O)OR_{4g}R_{4h}$;
$R_5$ is hydrogen, halogen, cyano, nitro, alkyl, alkenyl, alkynyl, heteroalkyl, aryl, heteroaryl, heterocycle, cycloalkyl, cycloalkenyl, —$OR_{5a}$, —$NR_{5b}R_{5c}$, —$SR_{5d}$, —$SO_2R_{5e}$, —$S(O)R_{3f}$, —$P(O)OR_{5g}R_{5h}$;
or $R_2$ and $R_3$ together with the atoms to which they are attached, $R_3$ and $R_4$ together with the atoms to which they are attached, or $R_4$ and $R_5$ together with the atoms to which they are attached, form a 5- or 6-membered saturated, partially unsaturated or fully unsaturated ring, the 5- or 6-membered ring optionally containing 1, 2 or 3 heteroatoms or heteroatom groups each independently selected from the group consisting of, N, S, NO, SO and $SO_2$ as ring members, the 5- or 6-membered ring optionally fused to an aryl, heteroaryl, heterocycle, or cycloalkyl, the 5- or 6-membered ring substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, or acyl;

$R_{1a}$, $R_{1b}$, $R_{1c}$, $R_{2a}$, $R_{2b}$, $R_{2c}$, $R_{2d}$, $R_{2e}$, $R_{2f}$, $R_{2g}$, $R_{2h}$, $R_{3a}$, $R_{3b}$, $R_{3c}$, $R_{3d}$, $R_{3e}$, $R_{3f}$, $R_{3g}$, $R_{3h}$, $_{4a}$, $R_{4b}$, $R_{4c}$, $R_{4d}$, $R_{4e}$, $R_{4f}$, $R_{4g}$, $R_{4h}$, $R_{5a}$, $R_{5b}$, $R_{5c}$, $R_{5d}$, $R_{5e}$, $R_{5f}$, $R_{5g}$, and $R_{5h}$, are each independently selected from the group consisting of hydrogen, alkyl, alkenyl, alkynyl, heteroalkyl, aryl, heteroaryl, heterocycle, cycloalkyl, and cycloalkenyl;
$R_{1x}$, $R_{2x}$, $R_{3x}$, $R_{4x}$, and $R_{5x}$ are each independently hydrogen or $C_1$-$C_{12}$alkyl;
—$NR_{1x}G^{10}$ is

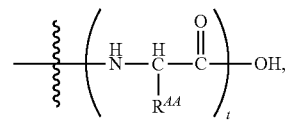

wherein $R^{AA}$ at each occurrence is independently hydrogen, alkyl, or alkyl substituted with a substituent selected from the group consisting of —OH, —$NH_2$, —SH, —$SCH_3$, phenyl, —COOH, —CO—$NH_2$,

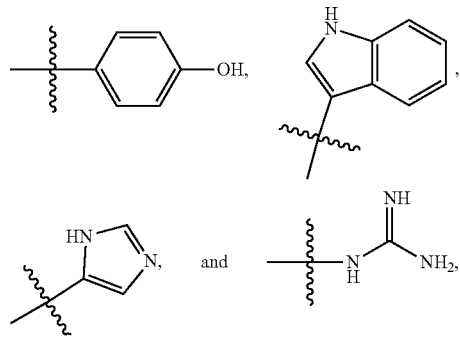

and t is 1-10; and
$W_1$ and $W_2$ are each independently selected from the group consisting of alkyl, alkenyl, alkynyl, alkoxy, heteroalkyl, aryl, heteroaryl, heterocycle, cycloalkyl, and cycloalkenyl;

wherein said alkyl, alkenyl, alkynyl, alkoxy, heteroalkyl, aryl, heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; and detecting luminescence;

wherein the transgenic animal expresses a luciferin-utilizing luciferase.

20. A method of detecting ATP in a sample comprising:
(a) adding to the sample a reagent composition comprising a compound of formula (I'):

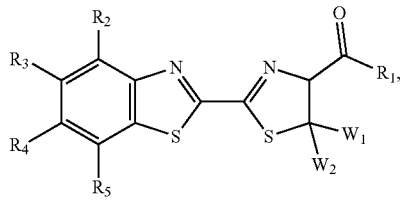

or a tautomer or a salt thereof, wherein

R₁ is hydrogen, halogen, alkyl, alkenyl, alkynyl, heteroalkyl, aryl, heteroaryl, heterocycle, cycloalkyl, cycloalkenyl, —OR$_{1a}$, —NR$_{1b}$R$_{1c}$ or —NR$_{1x}$G$^{10}$;

R₂ is hydrogen, halogen, cyano, nitro, alkyl, alkenyl, alkynyl, heteroalkyl, aryl, heteroaryl, heterocycle, cycloalkyl, cycloalkenyl, —OR$_{2a}$, —NR$_{2b}$R$_{2c}$, —SR$_{2d}$, —SO₂R$_{2e}$, —S(O)R$_{2f}$ or —P(O)OR$_{2g}$R$_{2h}$;

R₃ is hydrogen, halogen, cyano, nitro, alkyl, alkenyl, alkynyl, heteroalkyl, aryl, heteroaryl, heterocycle, cycloalkyl, cycloalkenyl, —OR$_{3a}$, —NR$_{3b}$R$_{3c}$, —SR$_{3d}$, —SO₂R$_{3e}$, —S(O)R$_{3f}$ or —P(O)OR$_{3g}$R$_{3h}$;

R₄ is hydrogen, halogen, cyano, nitro, alkyl, alkenyl, alkynyl, heteroalkyl, aryl, heteroaryl, heterocycle, cycloalkyl, cycloalkenyl, —OR$_{4a}$, —NR$_{4b}$R$_{4c}$, —SR$_{4d}$, —SO₂R$_{4e}$, —S(O)R$_{4f}$ or —P(O)OR$_{4g}$R$_{4h}$;

R₅ is hydrogen, halogen, cyano, nitro, alkyl, alkenyl, alkynyl, heteroalkyl, aryl, heteroaryl, heterocycle, cycloalkyl, cycloalkenyl, —OR$_{5a}$, —NR$_{5b}$R$_{5c}$, —SR$_{5d}$, —SO₂R$_{5e}$, —S(O)R$_{5f}$ or —P(O)OR$_{5g}$R$_{5h}$;

or R₂ and R₃ together with the atoms to which they are attached, R₃ and R₄ together with the atoms to which they are attached, or R₄ and R₅ together with the atoms to which they are attached, form a 5- or 6-membered saturated, partially unsaturated or fully unsaturated ring, the 5- or 6-membered ring optionally containing 1, 2 or 3 heteroatoms or heteroatom groups each independently selected from the group consisting of O, N, S, NO, SO and SO₂ as ring members, the 5- or 6-membered ring optionally fused to an aryl, heteroaryl, heterocycle, or cycloalkyl, the 5- or 6-membered ring substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl;

R$_{1a}$, R$_{1b}$, R$_{1c}$, R$_{2a}$, R$_{2b}$, R$_{2c}$, R$_{2d}$, R$_{2e}$, R$_{2f}$, R$_{2g}$, R$_{2h}$, R$_{3a}$, R$_{3b}$, R$_{3c}$, R$_{3d}$, R$_{3e}$, R$_{3f}$, R$_{3g}$, R$_{3h}$, R$_{4a}$, R$_{4b}$, R$_{4c}$, R$_{4d}$, R$_{4e}$, R$_{4f}$, R$_{4g}$, R$_{4h}$, R$_{5a}$, R$_{5b}$, R$_{5c}$, R$_{5d}$, R$_{5e}$, R$_{5f}$, R$_{5g}$, and R$_{5h}$, are each independently selected from the group consisting of hydrogen, alkyl, alkenyl, alkynyl, heteroalkyl, aryl, heteroaryl, heterocycle, cycloalkyl, and cycloalkenyl;

R$_{1x}$, R$_{2x}$, R$_{3x}$, R$_{4x}$, and R$_{5x}$ are each independently hydrogen or C$_1$-C$_{12}$alkyl;

—NR$_{1x}$G$^{10}$

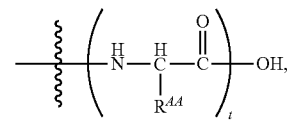

wherein R$^{AA}$ at each occurrence is independently hydrogen, alkyl, or alkyl substituted with a substituent selected from the group consisting of —OH, —NH₂, —SH, —SCH₃, phenyl, —COOH, —CO—NH₂,

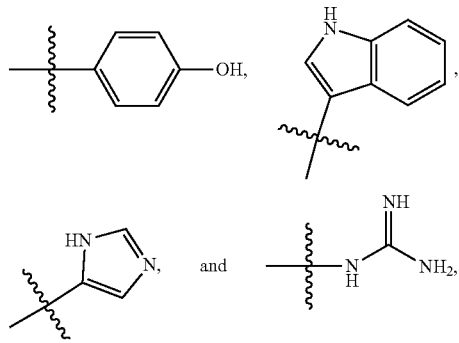

and t is 1-10; and

W₁ and W₂ are each independently selected from the group consisting of alkyl, alkenyl, alkynyl, alkoxy, heteroalkyl, aryl, heteroaryl, heterocycle, cycloalkyl, and cycloalkenyl;

wherein said alkyl, alkenyl, alkynyl, alkoxy, heteroalkyl, aryl, heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; and (b) detecting luminescence.

21. A kit comprising a compound of formula (I'):

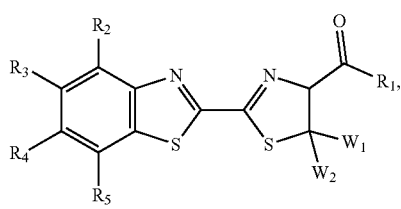

or a tautomer or a salt thereof, wherein
$R_1$ is hydrogen, halogen, alkyl, alkenyl, alkynyl, heteroalkyl, aryl, heteroaryl, heterocycle, cycloalkyl, cycloalkenyl, —$OR_{1a}$, —$NR_{1b}R_{1c}$, or —$NR_{1x}G^{10}$;
$R_2$ is hydrogen, halogen, cyano, nitro, alkyl, alkenyl, alkynyl, heteroalkyl, aryl, heteroaryl, heterocycle, cycloalkyl, cycloalkenyl, —$OR_{2a}$, —$NR_{2b}R_{2c}$, —$SR_{2d}$, —$SO_2R_{2e}$, —$S(O)R_{2f}$, or —$P(O)OR_{2g}R_{2h}$;
$R_3$ is hydrogen, halogen, cyano, nitro, alkyl, alkenyl, alkynyl, heteroalkyl, aryl, heteroaryl, heterocycle, cycloalkyl, cycloalkenyl, —$OR_{3a}$, —$NR_{3b}R_{3c}$, —$SR_{3d}$, —$SO_2R_{3e}$, —$S(O)R_{3f}$, or —$P(O)OR_{3g}R_{3h}$;
$R_4$ is hydrogen, halogen, cyano, nitro, alkyl, alkenyl, alkynyl, heteroalkyl, aryl, heteroaryl, heterocycle, cycloalkyl, cycloalkenyl, —$OR_{4a}$, —$NR_{4b}R_{4c}$, —$SR_{4d}$, —$S(O)_2R_{4e}$, —$S(O)R_{4f}$, or —$P(O)OR_{4g}R_{4h}$;
$R_5$ is hydrogen, halogen, cyano, nitro, alkyl, alkenyl, alkynyl, heteroalkyl, aryl, heteroaryl, heterocycle, cycloalkyl, cycloalkenyl, —$OR_{5a}$, —$NR_{5b}R_{5c}$, —$SR_{5d}$, —$SO_2R_{5e}$, —$S(O)R_{5f}$, or —$P(O)OR_{5g}R_{5h}$;
or $R_2$ and $R_3$ together with the atoms to which they are attached, $R_3$ and $R_4$ together with the atoms to which they are attached, or $R_4$ and $R_5$ together with the atoms to which they are attached, form a 5- or 6-membered saturated, partially unsaturated or fully unsaturated ring, the 5- or 6-membered ring optionally containing 1, 2 or 3 heteroatoms or heteroatom groups each independently selected from the group consisting of O, N, S, NO, SO and $SO_2$ as ring members, the 5- or 6-membered ring optionally fused to an aryl, heteroaryl, heterocycle, or cycloalkyl, the 5- or 6-membered ring substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl;
$R_{1a}$, $R_{1b}$, $R_{1c}$, $R_{2a}$, $R_{2b}$, $R_{2c}$, $R_{2d}$, $R_{2e}$, $R_{2f}$, $R_{2g}$, $R_{2h}$, $R_{3a}$, $R_{3b}$, $R_{3c}$, $R_{3d}$, $R_{3e}$, $R_{3f}$, $R_{3g}$, $R_{3h}$, $R_{4a}$, $R_{4b}$, $R_{4c}$, $R_{4d}$, $R_{4e}$, $R_{4f}$, $R_{4g}$, $R_{4h}$, $R_{5a}$, $R_{5b}$, $R_{5c}$, $R_{5d}$, $R_{5e}$, $R_{5f}$, $R_{5g}$, and $R_{5h}$, are each independently selected from the group consisting of hydrogen, alkyl, alkenyl, alkynyl, heteroalkyl, aryl, heteroaryl, heterocycle, cycloalkyl, and cycloalkenyl;
$R_{1x}$, $R_{2x}$, $R_{3x}$, $R_{4x}$, and $R_{5x}$ are each independently hydrogen or $C_1$-$C_{12}$alkyl;
—$NR_{1x}G^{10}$

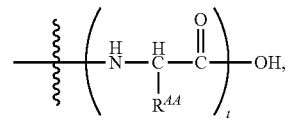

wherein $R^{AA}$ at each occurrence is independently hydrogen, alkyl, or alkyl substituted with a substituent selected from the group consisting of —OH, —$NH_2$, —SH, —$SCH_3$, phenyl, —COOH, —CO—$NH_2$,

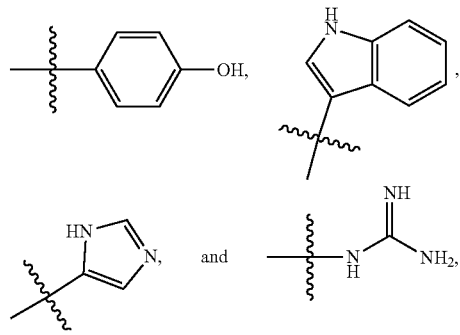

and t is 1-10; and
$W_1$ and $W_2$ are each independently selected from the group consisting of alkyl, alkenyl, alkynyl, alkoxy, heteroalkyl, aryl, heteroaryl, heterocycle, cycloalkyl, and cycloalkenyl;
wherein said alkyl, alkenyl, alkynyl, alkoxy, heteroalkyl, aryl, heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

22. The kit of claim 21, further comprising a luciferase.
23. The kit of claim 21, further comprising a buffer reagent.

* * * * *